United States Patent
Noguchi et al.

(10) Patent No.: US 6,650,409 B1
(45) Date of Patent: *Nov. 18, 2003

(54) SEMICONDUCTOR DEVICE PRODUCING METHOD, SYSTEM FOR CARRYING OUT THE SAME AND SEMICONDUCTOR WORK PROCESSING APPARATUS INCLUDED IN THE SAME SYSTEM

(75) Inventors: Minori Noguchi, Yokohama (JP); Yukio Kembo, Yokohama (JP); Hiroshi Morioka, Ebina (JP); Hidetoshi Nishiyama, Fujisawa (JP); Hideaki Doi, Oota-ku (JP); Masataka Shiba, Yokohama (JP); Yoshiharu Shigyo, Takasaki (JP); Kazuhiko Matsuoka, Tano-gun (JP); Kenji Watanabe, Oume (JP); Yoshimasa Ohshima, Yokohama (JP); Fumiaki Endo, Kodaira (JP); Yuzo Taniguchi, Kodaira (JP)

(73) Assignee: Hitachi, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/617,270

(22) Filed: Mar. 14, 1996

Related U.S. Application Data

(63) Continuation-in-part of application No. 08/535,777, filed on Sep. 28, 1995, which is a continuation of application No. 08/046,720, filed on Apr. 16, 1993, now Pat. No. 5,463,459, which is a continuation-in-part of application No. 07/679,317, filed on Apr. 2, 1991, now Pat. No. 5,233,191, and a continuation-in-part of application No. 07/778,363, filed on Oct. 17, 1991, now Pat. No. 5,274,434.

(30) Foreign Application Priority Data

Mar. 14, 1995 (JP) ............................................. 7-054291
Mar. 14, 1995 (JP) ............................................. 7-054298

(51) Int. Cl.$^7$ ................................................ G01N 21/89
(52) U.S. Cl. ................................ 356/237.3; 356/237.4; 438/6
(58) Field of Search ................................ 356/237, 239, 356/394, 336, 338, 237.1, 237.2, 237.3, 237.4, 237.5; 438/14, 16, 790, 905, 935, 706; 250/559.4, 559.41, 559.45

(56) References Cited

U.S. PATENT DOCUMENTS 4,433,951 A * 2/1984 Koch et al. .................. 414/217
4,670,126 A * 6/1987 Messer et al. ............... 204/298
4,766,324 A * 8/1988 Saadat et al. ................ 356/431

(List continued on next page.)

FOREIGN PATENT DOCUMENTS

| JP | 62-213112 | | 9/1987 |
| JP | 02039523 | * | 2/1990 |
| JP | A-2-170279 | | 7/1990 |

(List continued on next page.)

*Primary Examiner*—Hoa Q. Pham
(74) *Attorney, Agent, or Firm*—Antonelli, Terry, Stout & Kraus, LLP

(57) ABSTRACT

A semiconductor device producing method and a semiconductor device producing system employs a processing apparatus provided with a dust particle detecting apparatus. The dust particle detecting apparatus measures the condition of adhesion of dust particles adhering to a work at least before or after processing the work, manages the condition of incremental adhesion of dust particles to the work resulting from processing for each lot of works or for each work on the basis of the measured condition of adhesion of dust particles measured before or after processing the work, and determines the time when the processing apparatus is to be cleaned or the cycle of cleaning the processing apparatus on the basis of the managed condition of adhesion of dust particles.

49 Claims, 21 Drawing Sheets

U.S. PATENT DOCUMENTS

| | | | | |
|---|---|---|---|---|
| 4,962,063 A | * | 10/1990 | Maydan et al. | 437/228 |
| 5,038,048 A | | 8/1991 | Maeda et al. | 250/563 |
| 5,221,425 A | * | 6/1993 | Blanchard et al. | 156/643 |
| 5,233,191 A | | 8/1993 | Noguchi et al. | 250/306 |
| 5,255,089 A | * | 10/1993 | Dybas et al. | 358/101 |
| 5,274,434 A | | 12/1993 | Morioka et al. | 356/237 |
| 5,310,410 A | * | 5/1994 | Begin et al. | 29/25.01 |
| 5,463,459 A | * | 10/1995 | Morioka et al. | 356/237 |
| 5,942,672 A | * | 8/1999 | Harwell et al. | 73/1.07 |

FOREIGN PATENT DOCUMENTS

| | | |
|---|---|---|
| JP | A-3-44054 | 2/1991 |
| JP | A-3-285339 | 12/1991 |
| JP | A-4-56245 | 2/1992 |
| JP | A-4-152545 | 5/1992 |
| JP | 5-144918 | 6/1993 |
| JP | A-5-218163 | 8/1993 |
| JP | 5-259259 | 10/1993 |
| JP | A-6-258239 | 9/1994 |
| JP | 6-333791 | 12/1994 |
| JP | 7-37857 | 2/1995 |

* cited by examiner

FIG. 3a
FIG. 3b
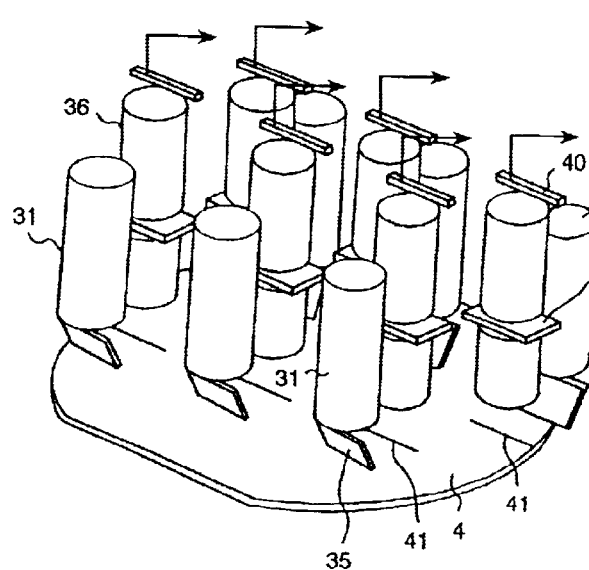
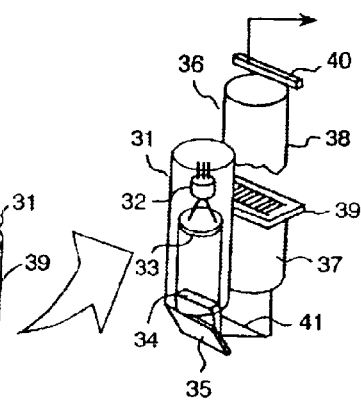
FIG. 4a
FIG. 4b
FIG. 4c
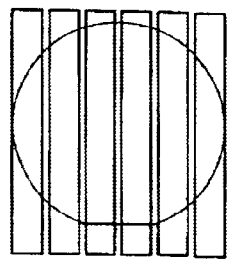
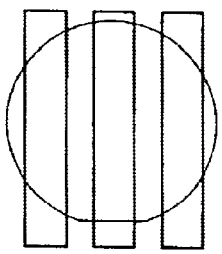
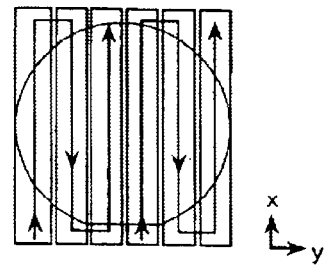

DUST PARTICLE MAP BEFORE PROCESSING

DUST PARTICLE MAP AFTER PROCESSING

INCREMENTAL DUST PARTICLE MAP

ACCUMULATED DATA

FIG. 28
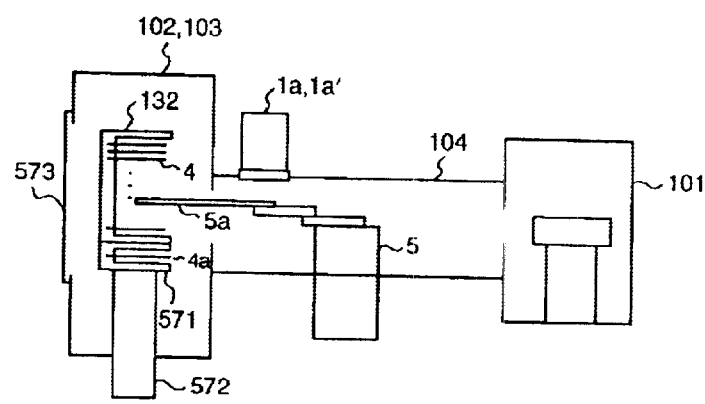
FIG. 29a      FIG. 29b      FIG. 29c
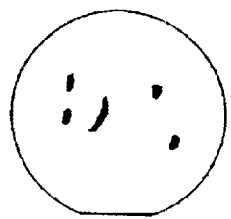   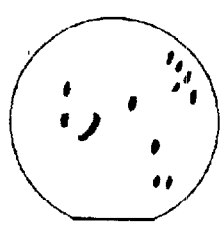   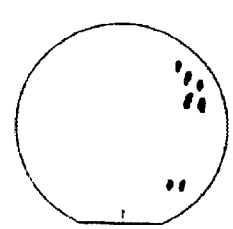

SEMICONDUCTOR DEVICE PRODUCING METHOD, SYSTEM FOR CARRYING OUT THE SAME AND SEMICONDUCTOR WORK PROCESSING APPARATUS INCLUDED IN THE SAME SYSTEM

CROSS REFERENCE TO RELATED APPLICATIONS

This is a continuation-in-part of U.S. application Ser. No. 08/535,577, filed Sep. 28, 1995, which is a continuation of U.S. application Ser. No. 08/046,720, filed Apr. 16, 1993, now U.S. Pat. No. 5,463,459, which is a continuation-in-part of Ser. 07/679,317, filed Apr. 2, 1991, now U.S. Pat. No. 5,233,191 and U.S. application Ser. No. 07/778,363, filed Oct. 17, 1991, now U.S. Pat. No. 5,274,434.

BACKGROUND OF THE INVENTION

The present invention relates to a semiconductor device producing method capable of processing semiconductor works at a high yield rate by a processing apparatus for processing a semiconductor work, such as a sputtering apparatus or a CVD apparatus for forming films on semiconductor substrates, such as semiconductor wafers and TFT substrates, an etching apparatus for patterning films, a resist coat forming apparatus, an exposure apparatus or a cleaning apparatus, by reducing dust particles adhering to semiconductor substrates or semiconductor works, a system for carrying out the same semiconductor device producing method, and a processing apparatus included in the same system.

Semiconductor device producing methods and systems for carrying out the same methods are disclosed in Japanese Patent Laid-open No. 5-218163 (corresponding to U.S. Pat. No. 5,463,459), Japanese Patent Laid-open No. 4-56245 (corresponding to U.S. Pat. No. 5,233,191), Japanese Patent Laid-open No. 4-152545 (corresponding to U.S. Pat. No. 5,274,434), Japanese Patent Laid-open No. 3-285339 (corresponding to U.S. Pat. No. 5,233,191), Japanese Patent Laid-open No. 3-44054 (corresponding to U.S. Application Ser. No. 07/908550), and Japanese Patent Laid-open No. 6-258239.

In these prior art techniques, however, careful consideration is not given to the reduction of dust particles adhering to semiconductor substrates, such as semiconductor wafers or TFT substrates, or semiconductor works on a processing apparatus, such as a sputtering apparatus or a CVD apparatuses for forming films on semiconductor substrates, etching apparatus for patterning films, a resist coat forming apparatus, an exposure apparatus or a cleaning apparatus, to produce semiconductor devices at a high yield rate.

SUMMARY OF THE INVENTION

It is an object of the present invention to provide a semiconductor device producing method capable of processing semiconductor works at a high yield rate by a processing apparatus, such as a sputtering apparatus or a CVD apparatus for forming films on semiconductor substrates, such as semiconductor wafers and TFT substrates, an etching apparatus for patterning films, a resist coat forming apparatus, an exposure apparatus or a cleaning apparatus, by reducing dust particles adhering to semiconductor substrates or semiconductor works, and a system for carrying out the same semiconductor device producing method.

Another object of the present invention is to provide a processing apparatus, such as a sputtering apparatus or a CVD apparatus for forming films on semiconductor substrates, such as semiconductor wafers and TFT substrates, an etching apparatus for patterning films, a resist coat forming apparatus, an exposure apparatus or a cleaning apparatus, capable of processing semiconductor works at a high yield rate by reducing dust particles adhering to semiconductor substrates or semiconductor works, and a system including the same processing apparatus.

With the fore going object in view, the present invention provides a semiconductor device producing method comprising: measuring the condition of adhesion of dust particles (foreign particles) adhering to a semiconductor work by a dust particle detecting apparatus incorporated into a processing apparatus before the semiconductor work is processed by the processing apparatus; measuring the condition of adhesion of dust particles adhering to the semiconductor work by the dust particle detecting apparatus after the semiconductor work has been processed by the processing apparatus; and processing the semiconductor work to produce a semiconductor device by the processing apparatus while managing a changing condition of adhesion of dust particles by comparing the condition of adhesion of dust particles before the semiconductor work is processed and the condition of adhesion of dust particles after the semiconductor work has been processed, by managing unit.

The present invention provides a semiconductor device producing method which gives an alarm when the generating state of dust particles is abnormally so that the processing apparatus can be delayed the time for cleaning or can be extended a cleaning cycle.

According to the present invention, in the aforesaid semiconductor device producing method, the delivery of the semiconductor work to the next process is controlled on the basis of the number of dust particles adhering to the semiconductor work by the processing apparatus.

According to the present invention, a semiconductor device producing method comprises generating an alarm when measured number of dust particles on wafers of a lot in process or wafers tends to increase with time, or the measured number of dust particles is changed with time to abnormally large.

According to the present invention, a semiconductor device producing method comprises:
registering a database specifying the relation between a dust particle distribution map showing distributions of dust particles adhering to semiconductor works obtained by analyzing known semiconductor works and causes of adhesion of the dust particles to the semiconductor works; comparing measured data of an abnormal semiconductor work with known data, and specifying a mode of occurrence of faults when the measured data of the abnormal semiconductor work is similar to the known data to curtail time between finding of abnormality and taking measures to cope with the abnormality.

According to the present invention, in the aforesaid semiconductor device producing method, a method of cleaning the processing apparatus (overall cleaning or part cleaning) is specified.

According to the present invention, in the aforesaid semiconductor device producing method, an instruction is given for further detection.

According to the present invention, a semiconductor device producing method uses an interface common to a plurality of various apparatuses or simple stages, mounts the interface on desired one of the plurality of various apparatuses to use a single detection head in combination with the plurality of various apparatuses or an individual detecting apparatus.

According to the present invention, a semiconductor device producing method checks the condition of adhesion of dust particles to a semiconductor work and detects a specific dust particle appearance mode.

According to the present invention, a semiconductor device producing system has composite functions including a film thickness measuring function and an ID read function.

According to the present invention, a semiconductor device producing method and a system for carrying out the semiconductor device producing method measure the condition (the number of adhering dust particles or a dust particle distribution map showing distribution) of dust particles adhering to a work before and after processing, by a dust particle detecting apparatus included in a processing apparatus, and process the work by the processing apparatus while managing the condition of adhesion of dust particles being obtained by comparing the measured condition of adhesion of dust particles adhering to the work before processing and that after processing, by a managing unit (CPU).

According to the present invention, a semiconductor device producing method and a system for carrying out the semiconductor device producing method measure the condition (the number of adhering dust particles or a dust particle distribution map) of adhesion of dust particles to a work (semiconductor substrate) before and after processing, by a dust particle detecting apparatus included in a processing apparatus, manage a generating condition for each lot or each wafer by a managing unit (CPU) when processing the work, in accordance with comparing the measured conditions of adhesion of dust particles to the work before and after processing, and process the works for production by using the processing apparatus while controlling the feed of works to the processing apparatus by the control unit on the basis of condition of adhesion of dust particles adhering to the work for each lot or each wafer.

According to the present invention, a semiconductor device producing method and a system for carrying out the semiconductor device producing method measure at least the condition (the number of adhering dust particles or a dust particle distribution map showing distributions of dust particles adhering to a work at least before or after processing or measures the condition (the number of adhering dust particles or a dust particle distribution map shown distributions) of dust particles adhering to a work before and after processing, manage the condition of adhesion of dust particles resulting from processing for each lot or each wafer on the basis of at least the measured condition of adhesion of dust particles adhering to the work before or after processing or on the basis of the result of comparison of the condition of adhesion of dust particles to the work before processing. and that after processing by a managing unit (CPU), control the time or cycle of cleaning the processing apparatus on the basis of the condition of adhesion of dust particles adhering to the work for each lot or each work, and process the work by the controlled processing apparatus for production.

According to the present invention, a semiconductor device producing method and a system for carrying out the semiconductor device producing method measure the condition of adhesion of dust particles adhering to a work for each lot or each work, give an alarm when the measured condition of adhesion of dust particles adhering to the work increases with time or is an abnormal condition beyond a control limit, and stop processing each lot or each work.

According to the present invention, a semiconductor device producing method and a system for carrying out the semiconductor device producing method measure at least the condition (the number of adhering dust particles or a dust particle distribution map) of adhesion of dust particles adhering to a work before or after processing or measure the condition of adhesion of dust particle adhering to a wafer before and after processing, manage the number of dust particles adhered to the work during processing for each lot or each wafer by a managing unit (CPU) on the basis of at least the measured condition of adhesion of dust particles to the work before or after processing or the result of comparison of the condition of adhesion of dust particles adhering to the work before and after processing, stop processing each lot or each work when the managed condition of adhesion of dust particles adhering to the work for each lot or each work increases with time or is an abnormal condition beyond a control limit, control the processing by a control means, and processes the work by the controlled processing.

According to the present invention, a semiconductor device producing method registers a database specifying the known relation between each of dust particle distribution maps and each of causes of adhesion of the dust particles corresponding to each fault modes on a processing apparatus, the known relation being obtained by analyzing past accumulated data, compares dust particle distribution data measured by a dust particle detecting apparatus with said known relation data, and specifies a mode of occurrence of fault by searching a dust particle distribution map being similar to the measured data.

According to the present invention, a semiconductor device producing method and.a system for carrying out the semiconductor device producing method register a database specifying the known relation between each of adhering dust particle distribution maps and each of causes of adhesion of the dust particles corresponding to each fault cleaning modes on a processing apparatus, the known relation being obtained by analyzing past accumulated data, compares dust particle distribution data measured by a dust particle detecting apparatus with said known relation data, and specify a method cleaning for the processing apparatus by searching a dust particle distribution map being similar to the measured data.

According to the present invention, a semiconductor device producing method and a system for carrying out the semiconductor device producing method register a database specifying the known relation between each of dust particle distribution maps and each of causes of adhesion of the dust particles corresponding to each fault modes on a processing apparatus, the known relation being obtained by analyzing past accumulated data, compares dust particle distribution data measured by a dust particle detecting apparatus with said known relation data, and give an instruction for further detecting dust particle distribution corresponding to fault mode by the dust particle detecting apparatus for the processing apparatus.

According to the present invention, a semiconductor device producing method and a system for carrying out the semiconductor device producing method measure the condition of adhesion of dust particles adhering to a work at least before or after processing, or before and after processing by a dust particle detecting apparatus, manage the condition of incremental adhesion of dust particles to the work resulting from processing for each lot or each wafer on the basis of the measured condition of adhesion of dust particles adhering to the work at least before or after processing, or on the basis of the result of comparison of condition of adhesion of dust particles adhering to the work before and after processing by a managing means, estimate causes of faults when the managed condition of adhesion of dust particles adhering to the work for each lot or each work increases with time or is an abnormal condition beyond a control limit from the measured condition of adhesion of dust particles adhering to the work on the basis of registered database specifying the relation between a dust particle distribution map for the work and causes of faults, and control processing by a control means to eliminate the causes of faults.

According to the present invention, a semiconductor device producing method and a system for carrying out the semiconductor device producing method measure the condition (the number of adhering dust particles or a dust particle distribution map) at least before or after processing, or the condition of adhesion of dust particles adhering to the work before and after processing, manage the condition of incremental adhesion of dust particles to the work resulting from processing on the basis of at least the measured condition of adhering dust particles before or after processing, or the result of comparison of the condition of adhesion of dust particles adhering to the work before and after processing for each lot or each wafer by a managing means, estimate causes of faults when the managed condition of adhesion of dust particles adhering to the work for each lot or each work increases with time or is an abnormal condition beyond a control limit from the measured condition of adhesion of dust particles adhering to the work on the basis of registered database specifying the relation between a dust particle distribution map for the work and causes of faults, and control processing by a control means to eliminate the causes of faults, and process the work under controlled processing conditions for production.

According to the present invention, a semiconductor device producing method and a system for carrying out the semiconductor device producing method measure the condition (the number of adhering dust particles or a dust particle distribution map) of dust particles adhering to a work or the condition of adhesion of dust particles adhering to a work before and after processing by a dust particle detecting apparatus included in a processing apparatus, manage the condition of incremental adhesion of dust particles to the work resulting from processing on the basis of the measured condition of adhering dust particles, or the result of comparison of the condition of adhesion of dust particles adhering to the work before and after processing for each lot or each wafer by a managing means, estimate cleaning conditions from the measured condition of adhesion of dust particles adhering to the work on the basis of a database showing the relation between the previously registered dust particle distribution map and cleaning conditions when the managed condition of adhesion of dust particles adhering to the work for each lot or each work increases with time or is an abnormal condition beyond a control limit, clean the processing apparatus according to the cleaning conditions by a cleaning means, process the work by the cleaned processing apparatus for production.

According to the present invention, a semiconductor device producing method and a system for carrying out the semiconductor device producing method measure the condition of adhesion of dust particles adhering to a work or the condition of adhesion of dust particles adhering to a work before and after processing by a dust particle detecting apparatus included in a processing apparatus, manage the condition of incremental adhesion of dust particles to the work resulting from processing on the basis of the measured condition of adhesion of dust particles to the work or the result of comparison of the condition of adhesion of dust particles adhering to the work before and after processing by a managing means for each lot or each wafer, specify the processing apparatus from the measured condition of adhesion of dust particles adhering to the work on the basis of a database showing the relation between a registered dust particle distribution map and the processing apparatus when the managed condition of adhesion of dust particles adhering to the work for each lot or each work increases with time or is an abnormal condition beyond a control limit, clean the specified processing apparatus by a cleaning means, and processes the work the cleaned processing apparatus for production.

According to the present invention, a processing apparatus is provided with a dust particle detecting apparatus comprising a detecting head having a plurality of sets each of an illuminating optical system that illuminates the surface of a work being conveyed through the transfer chamber of the processing apparatus by a handling mechanism to detect dust particles adhering to the work with a light beam projected so as to fall obliquely on the surface of the work, and a detecting optical system that receives scattered light scattered by dust particles on the work illuminated with the light beam by the illuminating optical system by a photoelectric converting means to detect the dust particles; and a signal processing means for processing signals provided by the photoelectric converting means of the detecting head to extract signals representing the dust particles.

According to the present invention, a processing apparatus is provided with a dust particle detecting apparatus that detects dust particles adhering to a work being conveyed through the transfer chamber of the processing apparatus by a handling mechanism.

According to the present invention, a processing apparatus is provided with a dust particle detecting apparatus that detects dust particles adhering to a work being conveyed through the transfer chamber of the processing apparatus by a handling mechanism through a transparent window formed in the top cover of the transfer chamber.

According to the present invention, a processing apparatus is provided with a dust particle detecting apparatus for detecting dust particles adhering to a work to be processed in a processing chamber, disposed in a buffer chamber.

According to the present invention, a processing apparatus is provided with a dust particle detecting apparatus for detecting dust particles adhering to a work being conveyed through the transfer chamber or the buffer chamber of the processing apparatus by a handling mechanism, and has a managing means for managing the condition of adhesion of dust particles adhering to the work in the processing apparatus detected by the dust particle detecting apparatus for each lot or each wafer.

According to the present invention, in the foregoing processing apparatus, the dust particle detecting apparatus comprises a detecting head having a plurality of sets each of an illuminating optical system that illuminates the surface of a work being conveyed through the transfer chamber of the processing apparatus by a handling mechanism to detect dust particles adhering to the work with a light beam projected so as to fall obliquely on the surface of the work, and a detecting optical system that receives scattered light scattered by dust particles on the work illuminated with the light beam by the illuminating optical system by a photoelectric converting means to detect the dust particles; and a signal processing means for processing signals provided by the photoelectric converting means of the detecting head to extract signals representing the dust particles.

According to the present invention, in the foregoing processing apparatus, the dust particle detecting apparatus comprises a detecting head having a plurality of sets each of an illuminating optical system that illuminates the surface of a work with a light beam projected so as to fall obliquely on the surface of the work, and a detecting optical system that receives scattered light scattered by dust particles on the work illuminated by the illuminating optical system by a photoelectric converting means to detect the dust particles; a signal processing means for processing signals provided by the photoelectric converting means to extract signals representing the dust particles; and a rotational position detecting optical system for detecting the rotational position of the orientation flat of the work or the direction in which chips are arranged.

According to the present invention, in the foregoing processing apparatus, the dust particle detecting apparatus comprises a detecting head having a plurality of sets each of an illuminating optical system that illuminates the surface of a work with a light beam projected so as to fall obliquely on the surface of the work, and a detecting optical system that receives scattered light scattered by dust particles on the work illuminated by the illuminating optical system by a photoelectric converting means to detect the dust particles; a rotational position detecting optical system for detecting the rotational position of the orientation flat of the work or the direction in which chips are arranged; and a processing means that corrects the rotational position of coordinates on the work on the basis of the rotational position of the orientation flat of the work or the direction in which chips are arranged detected by the rotational position detecting optical system, comparing the chips by using signals provided by the photoelectric converting means to extract signals representing the dust particles.

According to the present invention, in the foregoing processing apparatus, the dust particle detecting apparatus comprises a detecting head having a plurality of sets each of an illuminating optical system that illuminates the surface of a work with a light beam projected so as to fall obliquely on the surface of the work, and a detecting optical system that receives scattered light scattered by dust particles on the work illuminated by the illuminating optical system by a photoelectric converting means to detect the dust particles; a processing means for extracting signals representing the dust particles by processing signals provided by the photoelectric converting means; a rotational position detecting optical system for optically detecting the rotational position of the orientation flat of the work or the direction in which chips are arranged; an inclination detecting optical system for detecting the inclination of the surface of the work; and an inclination control mechanism for controlling the inclination of the detecting head to the work according to the inclination of the work detected by the inclination detecting optical system.

According to the present invention, in the foregoing processing apparatus, the dust particle detecting apparatus comprises a detecting head having a plurality of sets each of an illuminating optical system that illuminates the surface of a work with a light beam projected so as to fall obliquely on the surface of the work, and a detecting optical system that receives scattered light scattered by dust particles on the work illuminated by the illuminating optical system by a photoelectric converting means to detect the dust particles; a processing means for processing signals provided by the photoelectric converting means to extract signals representing the dust particles; a rotational position detecting optical system for detecting the rotational position of the orientation flat of the work or the direction in which chips are arranged; a height detecting optical system for detecting the height of the surface of the work; and a height control mechanism for controlling the height of the detecting head relative to the work according to the height of the work detected by the height detecting optical system.

According to the present invention, a processing apparatus is provided with a dust particle detecting apparatus that detects dust particles adhering to a work being conveyed through the transfer chamber or the buffer chamber of the processing apparatus by a handling mechanism; and a managing means for managing the condition of adhesion of dust particles adhering to the work in the processing apparatus detected by the dust particle detecting apparatus for each lot or each wafer, and controlling the time or the cycle to stop the processing operation of the processing apparatus or to clean the processing apparatus on the basis of the condition of adhesion of dust particles adhering to the work for the controlled lot or wafer.

As is apparent from the foregoing description, according to the present invention, abnormal adhesion of dust particles to a semiconductor substrate, such as a semiconductor wafer or a TFT substrate, in a processing apparatus, such as a sputtering apparatus and a CVD apparatus for forming films on semiconductor substrates, such as semiconductor wafers and TFT substrates, an etching apparatus for patterning films, a resist coat forming apparatus, an exposure apparatus or a cleaning apparatus, and semiconductor devices can be produced at a high yield rate.

According to the present invention, an alarm or the like is provided for feedback control when an abnormal adhesion of dust particles to a semiconductor substrate, such as a semiconductor wafer or a TFT substrate, occurs in a processing apparatus, such as a sputtering apparatus and a CVD apparatus for forming films on semiconductor substrates, such as semiconductor wafers and TFT substrates, an etching apparatus for patterning films, a resist coat forming apparatus, an exposure apparatus or a cleaning apparatus, the processing apparatus is cleaned entirely or partially when such a feedback signal is given, and the process conditions, such as conditions for gases, conditions for evacuation, temperature condition and voltage to be applied, to reduce an abnormal adhesion of dust particles to the wafer so that semiconductor devices can be produced at a high yield rate.

BRIEF DESCRIPTION OF THE DRAWINGS

The above and other objects, features and advantages of the present invention will become more apparent from the following description taken in connection with the accompanying drawings, in which:

FIG. 3(a) is a perspective view of a detecting unit (detecting heads) embodying the present invention;

FIG. 3(b) is an enlarged perspective view of one of the detecting heads shown in FIG. 3(a);

FIGS. 4(a), 4(b) and 4(c) are diagrammatic views showing the relation between the number of channels of a detection unit (detecting heads) embodying the present invention and a scanning method;

FIG. 28 is a diagrammatic view for assistance in explaining a dust particle detecting operation to be carried out by a processing apparatus in accordance with the present invention by using a mirror finished wafer installed in a detecting unit; and FIGS. 29(a), 29(b) and 29(c) are plan views for assistance in explaining a method of obtaining dust particle detection data by the processing apparatus of FIG. 28 by using a mirror finished wafer.

DETAILED DESCRIPTION OF THE PREFERRED EMBODIMENTS

Preferred embodiments of the present invention will be described hereinafter with reference to the accompanying drawings.

A first embodiment of the present invention will described with reference to FIGS. 1 to 5.

Figure 1:
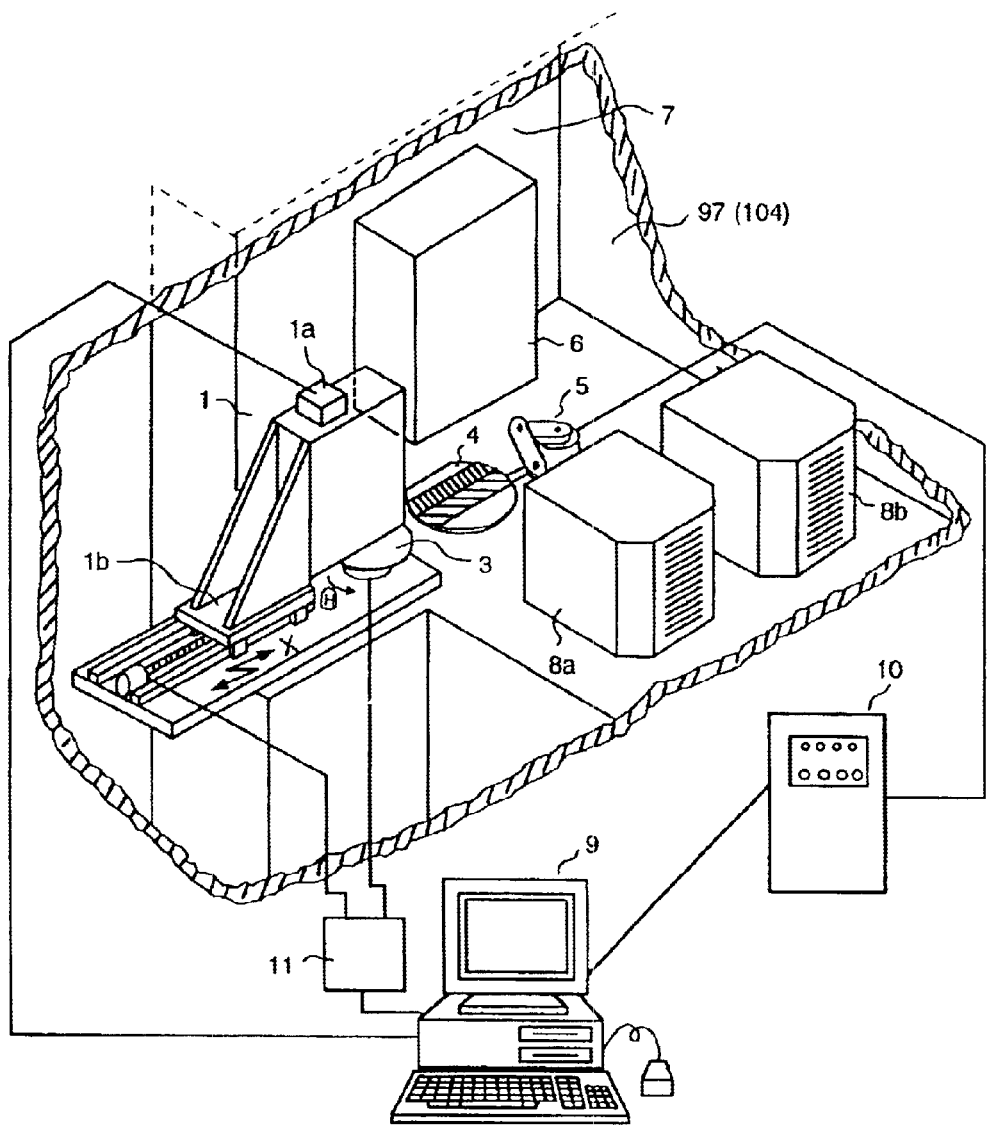
FIG. 1 is a partly cutaway perspective view of a processing apparatus in a preferred embodiment according to the present invention provided with a dust particle detecting apparatus.

A CVD apparatus for forming an insulating film or the like on a wafer 4, a sputtering apparatus of depositing a metal thin film or the like on a work 4, and an etching apparatus for etching a metal thin film or the like in a circuit pattern are representative processing apparatuses. FIG. 1 is a typical perspective view of the processing apparatus provided with a dust particle detecting unit 1. The processing apparatus comprises a processing chamber 7, and at least one work feed station 8a or 8b provided with a loader. The dust particle detecting unit 1 comprises a detecting head 1a, a scanning stage 1b, a Θ stage 3 which supports the work 4 and is capable of turning at least in the direction Θ to determine the rotational position of the work 4, a detection controller 11 for driving and controlling the scanning stage 1b and the Θ stage, and a data processing unit (CPU) 9. The dust particle detecting unit 1 need not necessarily be provided with the Θ stage because an image signal provided by a linear image sensor cam be processed electrically for rotational position correction. The condition of adhesion of dust particles (foreign particles) adhering to the work (wafer) 4 is measured by the dust particle detecting unit 1 before transporting the work 4 from the work feed station 8a or 8b through a buffer chamber 6 to the processing chamber 7 by a work handling mechanism 5, and then the work handling mechanism 5 transports the work 4 from the buffer chamber 6 to the processing chamber 7. The data processing unit (CPU) 9 of the dust particle processes measured results to obtain data indicating the condition of adhesion of dust particles adhering to the work 4, sends an alarm signal to a controller 10 for controlling the processing apparatus when the value exceeds a control limit value Mp. Then the controller 10 may control the processing apparatus not to process the work 4 in the processing chamber 7 and may control the work handling mechanism 5 to return the work 4 to the work feed station 8a or 8b to reduce the number of faulty works 4 processed by in the processing chamber 7 and to enhance the operation rate of the processing apparatus.

Figure 5A:
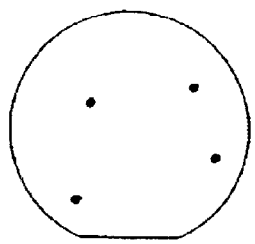
FIGS. 5(a), 5(b) and 5(c) are plan views of wafers, for assistance in explaining a method of calculating an incremental dust particle distribution map by a process embodying the present invention.
Figure 5B:
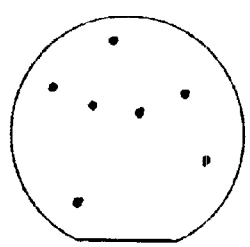
Figure 5C:
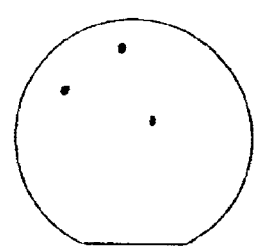

The work 4 transported to the processing chamber 7 is subjected to a film forming process or an etching process in the processing chamber 7. When returning the work 4 thus processed to the work feed station 8a or 8b by the work handling mechanism (robot mechanism) 5, the condition of adhesion of dust particles (foreign particles) adhering to the processed work 4 is measured by the dust particle detecting unit 1, and then the processed work 4 is stored in the work feed station 8a or 8b by the work handling mechanism 5. Measured data indicating the condition of adhesion of dust particles adhering to the work 4 is processed by a CPU 9a included in the data processing unit 9, and the processed data is added to database stored in a storage 9b or a hard disk, not shown. The CPU 9a of the processing unit 9 compares a preprocessing dust particle distribution map (FIG. 5(a)) showing the condition of adhesion of dust particles on the work 4 before processing, i.e., before the work 4 is transported to the processing chamber 7, and a postprocessing dust particle distribution map (FIG. 5(b)) showing the condition of adhesion of dust particles on the work 4 after processing, i.e., after the work 4 has been taken out from the processing chamber 7, for the number and the positions of dust particles, to obtain an incremental dust particle distribution map (5(c)) showing incremental dust particles increased by processing in the processing chamber 7. The incremental dust particle distribution map showing the number and the positions of the incremental dust particles is displayed on a monitor 9e or is outputted by an output unit 9f such as a printer; that is the preprocessing dust particle distribution map shown in FIG. 5(a) is subtracted from the postprocessing dust particle distribution map shown in FIG. 5(b) to obtain the incremental dust particle distribution map shown in FIG. 5(c). A method of subtracting the preprocessing dust particle distribution map from the postprocessing dust particle distribution map is disclosed in Japanese Patent Laid-open No. 2-170279 (corresponding to U.S. Pat. No. 5,038,048). The CPU 9a of the data processing unit 9 calculates the incremental dust particle distribution map, i.e., a dust particle distribution map showing dust particle data including the number and the sizes (large, medium and small) of dust particles deposited on the work 4 by the processing apparatus, and stores the incremental dust particle distribution map in the storage 9b or the hard disk, not shown.

A detecting head shown in FIGS. 3(a) and 3(b) and disclosed in Japanese Patent Laid-open No. 5-218163 (corresponding to U.S. Pat. No. 5,463,459), may be employed as the detecting head 1a. As shown in an enlarged perspective view in FIG. 3(b), an illuminating optical system 31 comprises a semiconductor laser 32 that emits a high-luminance (high-intensity) laser beam, a beam expanding optical system 33 for expanding the laser beam emitted by the semiconductor laser 32, a uniaxial condenser lens (cylindrical lens) 34 for condensing the laser beam expanded by the beam expanding optical system 33 in a flat laser beam (a linear shape laser beam), and a mirror 35 for reflecting the flat laser beam on the surface of the work 4 so that the flat laser beam falls on the surface of the work 4 at a small inclination. It is possible to scan the surface of the work 4 with a spot of a laser beam by a scanning optical system including a galvanomirror or the like instead of illuminating the surface of the work 4 with the flat laser beam by the uniaxial condenser lens. Although the laser beam must be moved at a high scanning speed for scanning by the scanning optical system of a complex construction when a spot of a laser beam is used, the beam expanding optical system is unnecessary and a semiconductor laser that emits a high-luminance (high-intensity) laser beam can be used. A detecting optical system 36 comprises telecentric optical systems 37 and 38 having a large field number (an NA of 0.4 to 0.6) for condensing scattered light scattered by the surface of the work 4 illuminated by the flat laser beam, a variable spatial filter 39 disposed substantially on the Fourier transform plane between the telecentric optical systems 37 and 38, and a linear image sensor 40. Light scattered by the edges of the circuit pattern formed on the surface of the work 4 or the spatial frequency of the repetitive circuit pattern is filtered by the variable spatial filter 39 to make only the light scattered by dust particles fall on the linear image sensor 40. As shown in FIG. 3(a), the detecting head 1a is provided with six sets each of the illuminating optical system 31 and the detecting optical system 36, disposed in a zigzag arrangement so that the substantially entire surface of the work 4 can be scanned when the controller 11 controls the scanning stage 1b to move the detecting head 1a along the x-axis. Therefore, when the detecting head 1a is moved relative to the work 4 along the x-axis for one scanning cycle, the entire surface of the work 4 can be scanned to detect the condition of adhesion of dust particles adhering to the work 4 as shown in FIG. 4(a).

When the detecting head 1a is provided with three sets each of the illuminating optical system 31 and the detecting optical system 36, and the detecting head 1a is moved relative to the work along the x-axis for one scanning cycle, most regions of the surface of the work 4 can be scanned and some regions of the same cannot be scanned as shown in FIG. 4(b). The detecting head 1a provided with three sets each of the illuminating optical system 31 and the detecting optical system 36 is simple in construction and can be moved at a high speed for quick scanning.

When the detecting head 1a is provided with two sets each of the illuminating optical system 31 and the detecting optical system 36, the detecting head 1a is moved along the x-axis relative to the work 4 for three scanning cycles and the optical head 1a is fed along the y-axis at every completion of one scanning cycle, the entire surface of the work 4 can be inspected for dust particles as shown in FIG. 4(c). Although this detecting head 1a is provided with only two sets of each of the illuminating optical system 31 and the detecting optical system 36, a scanning mechanism of a complex construction is necessary for moving the detecting head 1a and inspection takes much time because the detecting head 1a must be moved along the x-axis for three scanning cycles and fed along the y-axis.

Figure 2:
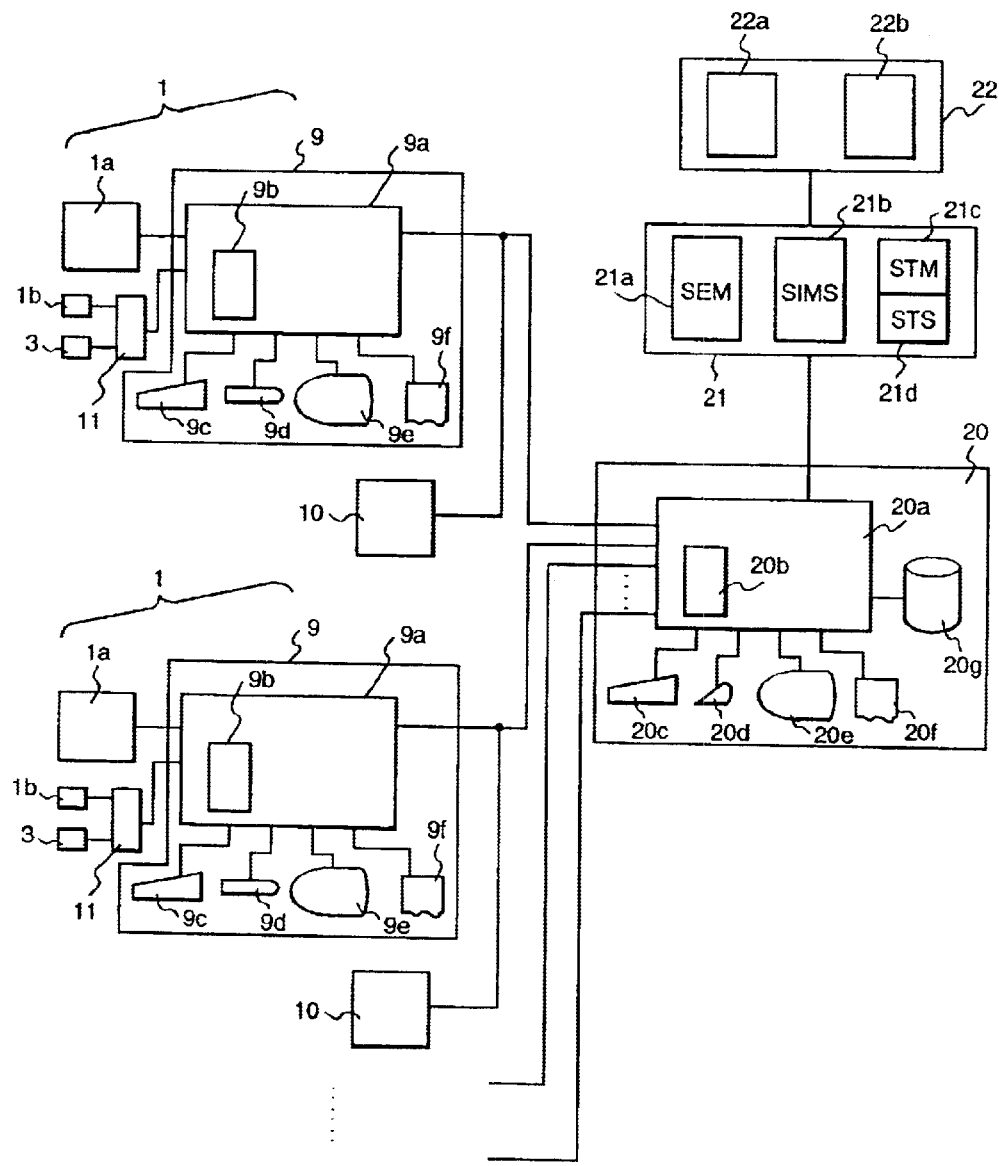
FIG. 2 is a general block diagram of a system in a preferred embodiment according to the present invention.

FIG. 2 shows a system comprising a plurality of dust particle detecting apparatuses 1, a plurality of controllers 10, which receives signals representing the pressure of the process gas, the temperature of the work (wafer) 4 and the like, for controlling processing apparatuses, an inspecting apparatus 22 comprising a dust particle inspecting apparatus 22a and a pattern inspecting apparatus 22b, an analyzing apparatus 21 comprising a scanning electron microscope (SEM) 21a, a secondary ion mass spectrometer (SIMS), a scanning tunnel microscope (STM) 21c and a spectrometer (STS) 21d, and a dust particle data analyzing computer 20.

The dust particle data analyzing computer 20 comprises a CPU 20a having a memory 20b, a keyboard 20c for entering data, a mouse 20d, a display 20e for displaying the results of dust particle analysis, an abnormal processing apparatus, an abnormal lot and an abnormal work for which an alarm must be given, an output unit 20f such as a printer, for delivering information representing the results of dust particle analysis, an abnormal processing apparatus, an abnormal lot and an abnormal work for which an alarm must be given, and an external storage (hard disk) 20g storing the relation between the condition of appearance of dust particles in each lot (for example twenty works) or on each work, and estimated or confirmed causes of appearance of dust particles. The dust particle data analyzing computer 30 receives data from a plurality of dust particle detecting apparatuses 1 and a plurality of controllers 10 for controlling the processing apparatuses provided with the dust particle detecting apparatus, and information about the lot or the work in which the data representing dust particles is beyond control limits $M_p$ and $M_q$, results of minute analysis performed by the detecting apparatus 22 and the analyzing apparatus 21, and estimated causes of faults entered by operating the keyboard 20c. The relation between the condition of appearance of dust particles in each lot or on each work processed by each processing apparatus and estimated or confirmed causes of appearance of dust particles is stored in the external storage (hard disk) 20g.

A second embodiment of the present invention will be described hereinafter with reference to FIGS. 1, 2 and 6.

Figure 6:
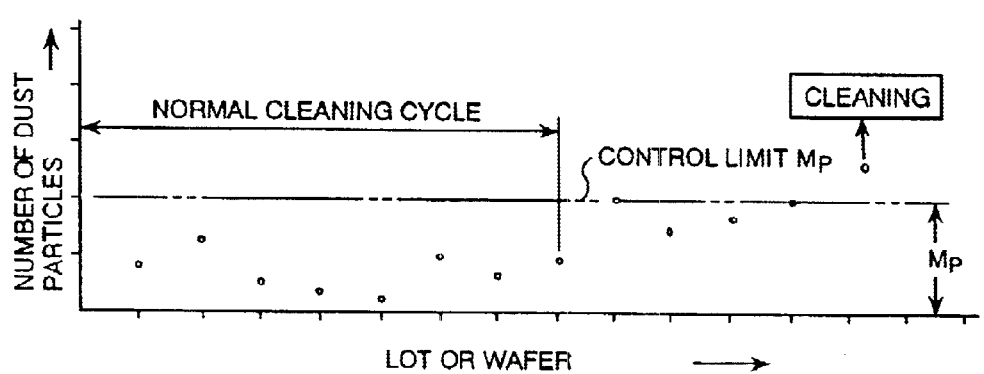
FIG. 6 is a graph showing the number of dust particles detected in a lot or on a wafer by the present invention.

FIG. 6 shows the relation between processed works 4 or lots, and the measured numbers of dust particles on works 4 or in lots processed by a film forming apparatus as a processing apparatus. The film forming apparatus supplies monosilane gas ($SiH_4$) and phosphine gas ($PH_3$) into a processing chamber to deposit a film on a work 4 by chemical reactions. The deposition of the product of the chemical reactions on the surfaces of walls defining the processing chamber increases with time, comes off the surface of the walls and falls on the work 4 to make the work 4 faulty. Therefore, the processing chamber is cleaned periodically by plasma cleaning.

The periodic plasma cleaning of the processing chamber reduces the efficiency of the film forming apparatus because the film forming apparatus is inoperative during plasma cleaning. The adhesion of dust particles to the work 4 is detected substantially continuously by the dust particle detecting apparatus 1 shown in FIG. 1, the CPU 9a of the data processing unit 9 monitors the number of dust particles adhering to the work 4 for a lot of, for example, twenty works or for each work 4, and gives an alarm to the display 9e or the controller 10 for controlling the processing apparatus if the number of dust particles tends to increases even if the number of dust particles adhering to the work 4 is below the control limit $M_p$ to request cleaning the processing apparatus. On the other hand, the CPU 9a of the data processing unit 9 monitors the number of dust particles adhering to works of each lot of, for example, twenty works, or to each work, and gives an alarm to the display 9e of the controller 10 for controlling the processing apparatus when the number of dust particles is greater than the control limit $M_p$ to request cleaning the processing apparatus. Thus, the processing apparatus is cleaned only when the operation of the same is truly abnormal and the periodic cleaning of the processing apparatus is not carried out so that the efficiency of the processing apparatus is enhanced.

Although the data processing unit 9 of the dust particle detecting apparatus 1 monitors the number of dust particles adhering to works for each lot or each work in the foregoing embodiments, the dust particle data analyzing computer 20 connected to the plurality of dust particle detecting apparatuses 1 may monitor the numbers of dust particles in each lot or on each work on the data representing the condition of adhesion of dust particles on works and provided by the data processing units 9 of the dust particle detecting apparatuses 1 and may give an alarm to the data processing units 9 of the dust particle detecting apparatuses or to the controllers 10 for controlling the processing apparatuses.

A third embodiment of the present invention will be described with reference to FIGS. 1, 2 and 7.

Figure 7:
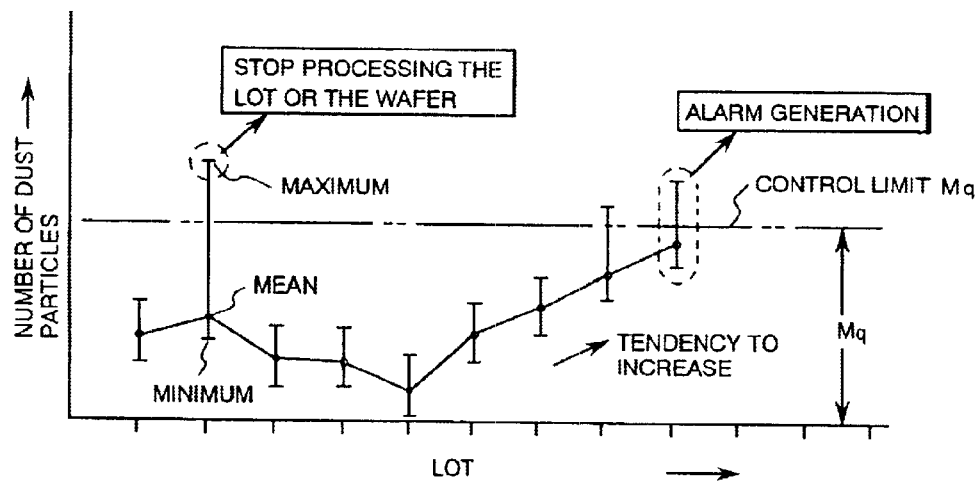
FIG. 7 is a graph showing a maximum, a minimum and a mean values of the number of dust particles in a lot, in accordance with the present invention.

FIG. 7 shows the relation between the measured number of dust particles (the mean of the maximum and the minimum number of dust particles on works ) on works (wafers) 4 measured by a dust particle detecting apparatus 1 of FIGS. 1 and 2 and lots of works 4 processed by a film forming apparatus as a processing apparatus by way of example. When the maximum number of dust particles on a work of a lot of, for example, twenty-five works measured by the CPU 9a of the data processing unit 9 of the dust particle detecting apparatus 1 is below the dust particle control limit $M_q$, the lot of works is delivered from the work feed station 8a or 8b to the next process for further processing. When the maximum number of detected dust particles on a work on a lot is greater than the dust particle control limit $M_q$, the works 4 included in the lot are taken out from the work feed station 8a or 8b, the dust particles adhering to the works 4 are detected by the operator and, if it is decided that the dust particles do not cause faults in the works 4, the works 4 are delivered to the next process by the work feed station 8a or 8b. The dust particle data analyzing computer 20 examines faulty works 4 or the lot for fault analysis on the basis of the information representing the condition of appearance of dust particles and causes of faults and stored in the hard disk 20g to elucidate causes of the dust particles and to improve the film forming apparatus. When the successive maximum numbers of dust particles or the successive means of the maximum and the minimum number of dust particles are smaller than but very close to the dust particle control limit $M_q$, or the numbers of dust particles in successive lots tend to increase, the data processing unit 9 of the dust particle detecting apparatus 1 gives an alarm to the display 9e or the controller 10 for controlling the processing apparatus.

A fourth embodiment of the present invention will be described with reference to FIGS. 1, 2 and 8.

Figure 8:
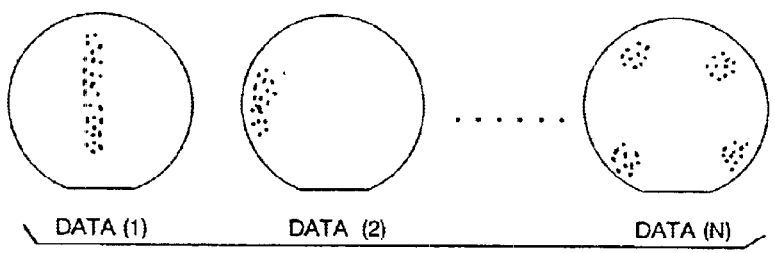
FIG. 8 is a view for assistance in explaining a method of estimating causes of abnormal appearance of dust particles on the basis of the analysis of past cases in accordance with the present invention.
Figure 8:
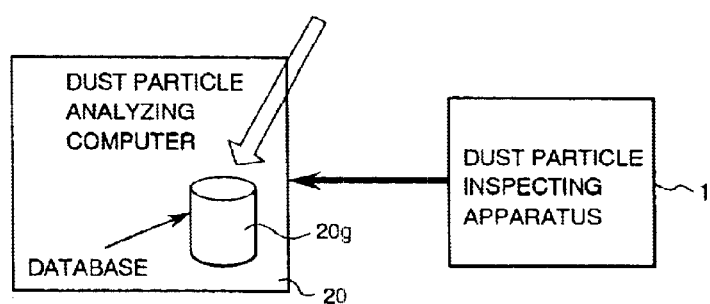

FIG. 8 shows a system for inspecting a work (wafer) 4 by the dust particle detecting apparatus 1 of FIG. 1 and analyzing abnormal work 4 by comparing data representing the condition of abnormality with previously stored data. The system comprises the dust particle detecting apparatus 1, and a dust particle data analyzing computer (workstation (W/S)) 20 having a database 20g. The dust particle detecting apparatus 1 measures the number of dust particles adhering to a work (wafer), registers data on abnormal works (dust particle distribution map, the number of detected dust particles) in the database 20g, and registers causes of faults in analyzed abnormal works 4 and measures taken to remove the faults additionally by the input unit 9c of the data processing unit 9 or the keyboard 20c connected to the dust particle data analyzing computer 20 in the data of the dust particle distribution maps registered in the database 20g of the dust particle data analyzing computer 20. Thus, data on abnormal works 4 are registered in the database 20g every time the data is obtained. When measured data on the work (wafer) 4 is beyond the control limits $M_p$ and $M_q$ determined on the basis of accumulated data, a map showing the distribution of dust particles is compared with previously stored dust particle distribution data (1) representing a band-shaped distribution of dust particles in the central portion of a work, previously stored dust particle distribution data (2) representing a concentrated distribution of dust particles in a left portion of a work, and stored dust particle distribution data (N) representing the distribution of dust particles in four portions in the periphery of a work, to find a stored dust particle distribution data obtained by past analysis and resembling the distribution of dust particles on the work 4 in process, causes of dust particles and measures taken to reduce dust particles, which are stored in the database 20g, corresponding to the selected stored dust particle distribution data are displayed on the display 20e, delivered by the output unit 20f or fed back to the controller 10 for controlling the processing apparatus. When determining the distribution of dust particles on a work 4, aggregates of dust particles by are enclosed by circles of a radius r or rectangles of a×b, respectively. and the distribution of dust particles can be expressed by the distances between the center of the work and the centers of gravity of the aggregates of dust particles, and the size of two-dimensional extension of the aggregates, such as the radius r of the circles when the aggregates of dust particles are enclosed by the circles or a/2×b/2 when the aggregates of dust particles are enclosed by rectangles of a×b. The aggregates of dust particles in each lot or each work thus classified are compared with causes of faults and measures taken to reduces faults.

A fifth embodiment of the present invention will be described hereinafter with reference to FIGS. 1, 2 and 9.

Figure 9:
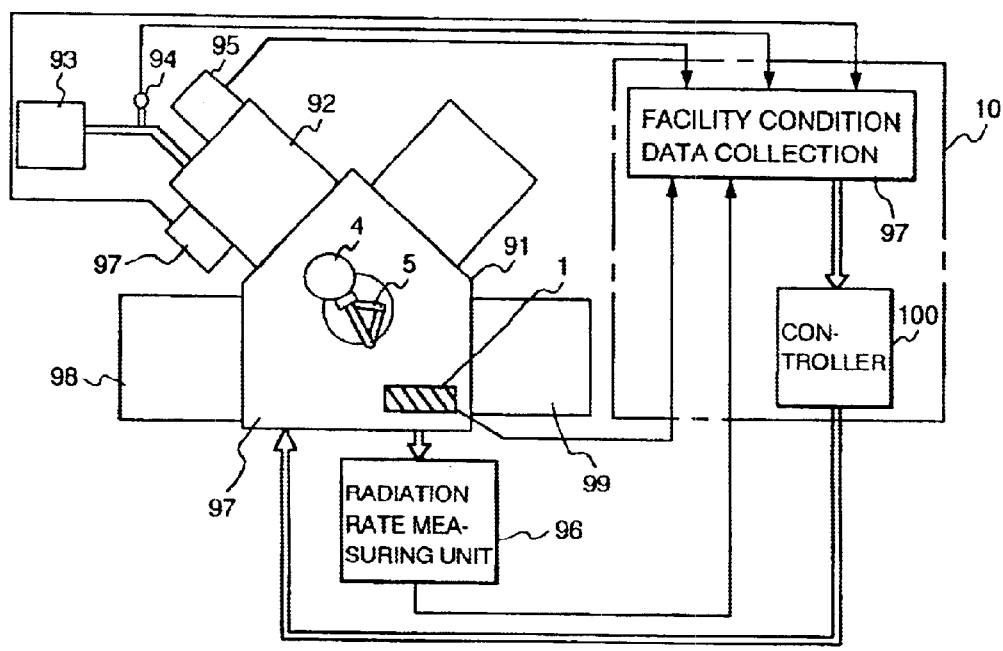
FIG. 9 is a block diagram of a processing apparatus, in another embodiment according to the present invention, different from that shown in FIG. 1, provided with a dust particle detecting apparatus.

FIG. 9 is a typical view showing the condition and control of a processing apparatus.

As shown in FIG. 9, a processing apparatus 91 comprises a flow measuring unit 94 for measuring the flow rate of a gas supplied from a gas source 93 into a processing chamber 92, a gas pressure measuring unit 95 for measuring the pressure in the processing chamber 92 or the vacuum in the processing chamber 92, a radiation rate measuring unit 96 for measuring radiation heat rate on the basis of the quantity of radiation heat from a work of a known temperature, a work temperature measuring unit 97 for measuring the actual temperature of the work on the basis of a radiation heat rate determined by the radiation heat rate measuring unit 96 and the quantity Q of radiation heat from the work in process, and the dust particle detecting apparatus 1 for inspecting a work 4 to be transported through a transfer chamber 97 from a loading chamber 98 to the processing chamber 92 or from the processing chamber 92 to an unloading chamber 99 by a work handling mechanism 5. Generally, the processing apparatus receives processing data representing processing conditions and processes the work according the processing data. The data on the condition of the processing apparatus during operation, such as a vacuum or a gas pressure measured by the gas pressure measuring unit 95, a flow rate of the gas measured by the flow measuring unit 94 and the temperature of the work measured by the work temperature measuring unit 97, are given to the controller 10 or a facility condition data collecting system included in the data processing unit 9 of the dust particle detecting apparatus 1, the facility condition data collecting system 97 combines the results of measurement of the processed work 4 by the dust particle detecting apparatus 1 (condition of appearance of dust. particles, the number of dust particles (foreign particles) in each lot or on each work) with the data on the condition of the processing apparatus, calculates the relation between the condition of the processing apparatus and the condition of appearance of dust particles when the processing is completed or before and after processing, when the gas pressure in the processing chamber 92 changed, when the flow rate of the gas being supplied into the processing chamber 92 changed and when the temperature of the work changed, and accumulates data thus obtained. The controller 10 estimates causes of adhesion of an abnormally large number of dust particles to the work on the basis of the measured condition of appearance of dust particles measured by the dust particle detecting apparatus 1 and the accumulated data representing the relation, and provides data on the causes of faults together with an alarm. Naturally, the causes of faults may be estimated by using data stored on the hard disk 20g of the dust particle data analyzing computer 20. Indicated at 100 is a controller that carries out control operations for controlling the processing apparatus 91 and the work handling mechanism 5. The controller 100 may be included in the controller 10 or may be an external controller when the controller 10 is included in the data processing unit 9.

The processing apparatus may be constructed so as to process the facility condition data collecting system 97 by the data processing unit 9 of the dust particle detecting apparatus 1 and the data on the relation may be accumulated on the memory 9b or a hard disk, not shown. In this case, causes of faults may be estimated on the basis of the measured condition of appearance of dust particles measured by the dust particle detecting apparatus 1 and the data on the relation accumulated in the memory 9b or the hard disk, not shown, when an abnormally large number of dust particles are produced, and the causes may be provided together with an alarm.

Figure 10A:
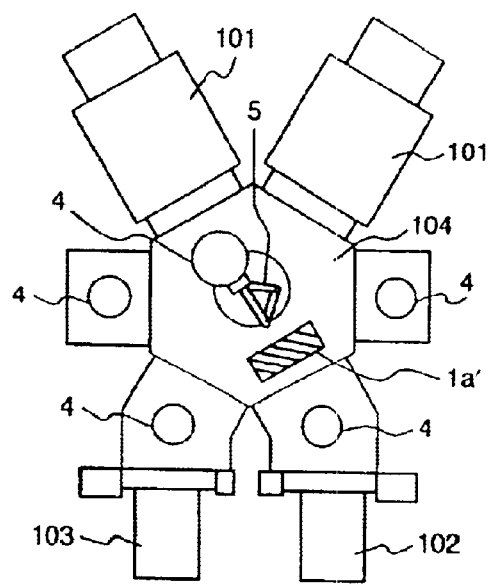
FIG. 10(a) is a plan view of a processing apparatus in a further embodiment according to the present invention, different from those shown in FIGS. 1 and 9, provided with a dust particle detecting apparatus.

A sixth embodiment of the present invention will be described hereinafter with reference to FIGS. 1, 2, 9 and 10. FIG. 10(a) shows a film forming apparatus provided with an on-machine dust particle detecting apparatus (on-machine dust particle monitor) 1. The film forming apparatus comprises a loading unit (L) 102, an unloading unit (U/L) 103, a transfer chamber 104, a reaction chamber 101, and a work handling mechanism 5 disposed in the transfer chamber 104. A detecting head 1a' for on-machine dust particle monitoring included in the dust particle detecting apparatus 1 is disposed in the upper portion of the transfer chamber 104. The work handling mechanism 5 receives a work 4 from the loading unit 102 and transports the work 4 from the loading unit 102 to the reaction chamber 101. The work 4 processed in the reaction chamber 101 is transported from the reaction chamber 101 to the unloading unit 103 by the work handling mechanism 5. While the processed work 4 is being transported from the reaction changer 101 to the unloading unit 103 by the work handling mechanism 5, the surface of the work 4 is monitored (inspected) by the detecting head 1a'.

Although this embodiment monitors the surface of the processed work 4, the surface of the work 4 may be monitored before processing the work 4 or may be monitored before and after processing.

Figure 10B:
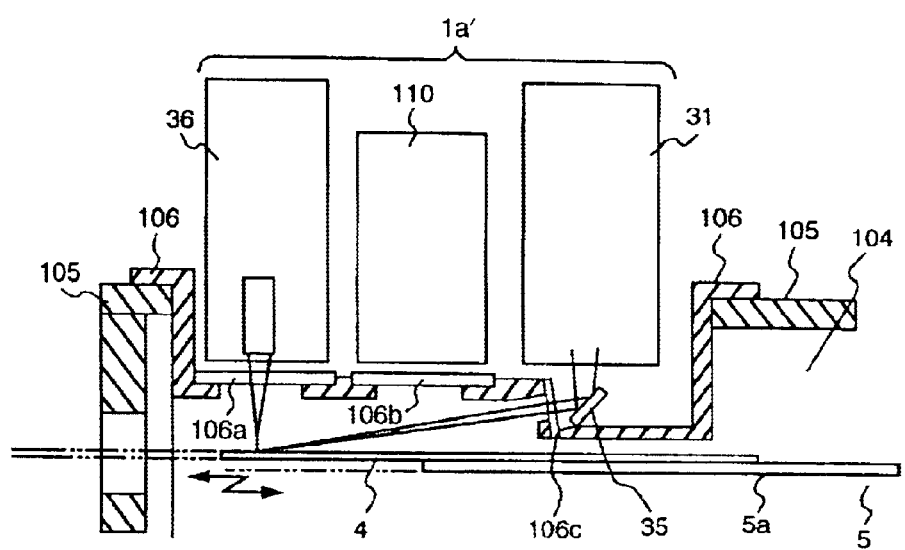
FIG. 10(b) is a fragmentary front view of the processing apparatus of FIG. 10(a)

FIG. 10(b) is a sectional view of the detecting head 1a' for on-machine dust particle monitoring. The transfer chamber 104 is evacuated. While the work 4 is being moved through the transfer chamber 104 by the handling arm 5a of the work handling mechanism 5, the detecting head 1a' disposed in the upper portion of the transfer chamber 104 monitors (inspects) the work 4. The detecting head 1a' is mounted on a vacuum-oriented standard flange 106. The detecting head 1a' comprises an illuminating optical system 31, a detecting optical system 36 and a work rotational position detecting system 110, which will be described later in detail. The rotational position of the work 4 is detected by the work rotational position detecting system 110, and the rotational position of the work 4 is corrected by image processing software, and the surface of the work 4 illuminated by the illuminating optical system 31 is monitored (inspected) by the detecting optical system 36. An illuminating part 106*a*, a detecting part 106*b* and a detecting part 106*c* of the vacuum-oriented standard flange 106 are transparent parts. A mirror 35 may be mounted on the vacuum-oriented standard flange 106.

Although this embodiment monitors (inspects) the work 4 through the vacuum-oriented standard flange 106, the detecting head 1*a*' may be miniaturized and may be disposed within the transfer chamber 104, i.e., in a vacuum atmosphere.

A seventh embodiment of the present invention will be described hereinafter with reference to FIGS. 11 and 12.

Figure 11:
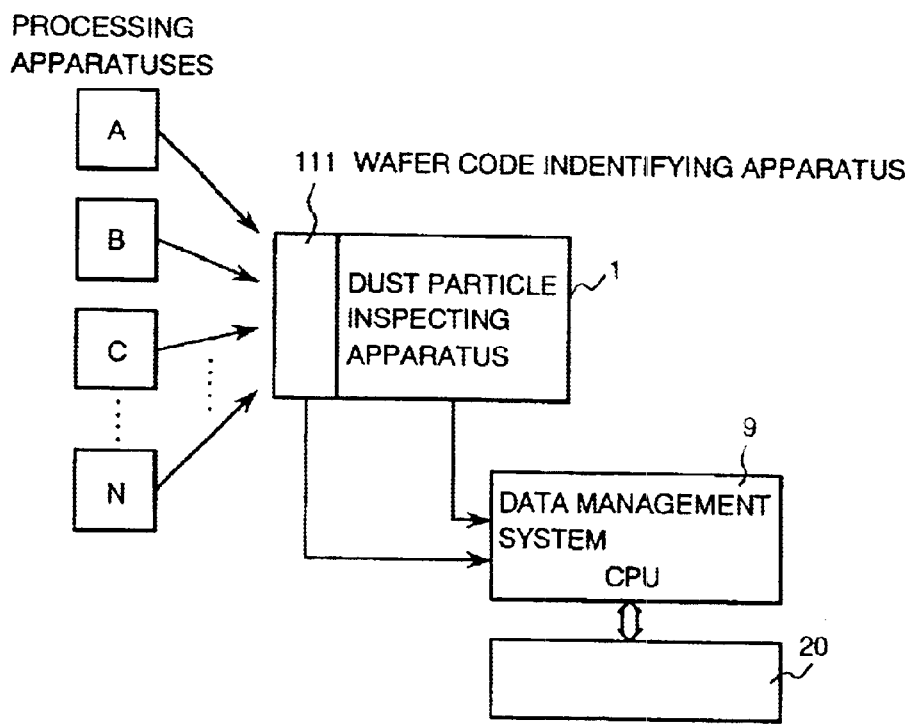
FIG. 11 is a block diagram of a system including a dust particle detecting apparatus in accordance with the present invention provided with a wafer code identifying device.
Figure 12:
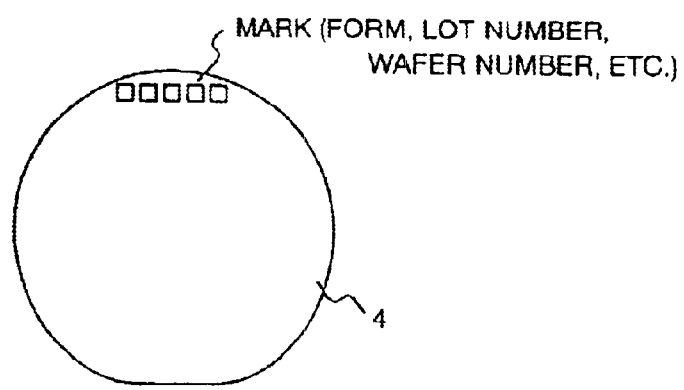
FIG. 12 is a plan view of a wafer on which an identification code is printed in accordance with the present invention.

As shown in FIG. 11, a dust particle detecting apparatus 1 is provided with a work identifying device 111 for reading a product form, or lot number and work number printed on a work or indicated by a bar code. The work identifying device 111 comprises a character reading optical system, not shown, and a character identifying unit, not shown. The work identifying device 111 is disposed at a work feed station for feeding a work to the dust particle detecting apparatus 1 or at the measuring station of the dust particle detecting apparatus 1 to read characters indicating, for example, a product form, a lot number and a work number printed on the work 4. The work 4 is inspected for dust particles by the dust particle detecting apparatus 1. The work data printed on the work 4 and measured data on dust particles and the like are transferred to a data processing unit 9. Thus, the condition of adhesion of dust particles to the works 4 can be controlled for each lot and each work. These data may be stored in a hard disk 20*g* and controlled by a dust particle data analyzing computer 20 and may be fed back to the controllers 10 of processing apparatuses A to N.

When the processing apparatuses are of the same type, the data can be controlled for each of the processing apparatuses A to N by designating the processing apparatus processed the work by an inspection condition determined by the dust particle detecting apparatus 1. Consequently, it is easily known that, for example, the works processed by the processing apparatus A have each a small number of dust particles whereas works processed by the processing apparatus B have each a large number of dust particles, and the data processing unit 9 is able to find out easily the abnormal processing apparatuses.

An eighth embodiment of the present invention will be described hereinafter.

A dust particle detecting apparatus 1 may be disposed at the exit of a work stocker for containing a plurality of work cassettes. The dust particle detecting apparatus inspects a work taken out from the work cassette by a work handling mechanism, not shown, which may be similar to the work handling mechanism 5, included in the dust particle detecting apparatus 1. A data processing unit 9 processes measured data, and data provided by the data processing unit 9 is stored in a memory 9*b* or a hard disk, not shown. These data may be stored on a hard disk 20*g* by a dust particle data analyzing computer 20.

The data processing unit 9 controls the storage/delivery of work cassette (not shown) and the results of measurement of dust particles. Wafers 4 not to be subjected to inspection after processing are inspected and dust particles adhering thereto are measured before putting the same into the work stockers. Therefore, operations for processing the works can be started without delay and the time necessary for processing the works can be curtailed. The data processing unit 9 controls delivering the processed works to the next process not to deliver the works to which an abnormally large number of dust particles are adhering to prevent the further processing of faulty works.

A ninth embodiment of the present invention will be described hereinafter with reference to FIGS. 13 to 15.

A method of correcting the rotational position of a work (wafer) will be described. A work rotational position detector 110 (FIG. 10) is disposed near the detecting head 1*a* shown in FIG. 1 or the detecting head 1*a*' shown in FIG. 10. The rotational position of a wafer detected by the work rotational position detector 110 is corrected mechanically by the Θ-stage 3, by the work handling mechanism 5 when the work handling mechanism 5 has a rotary hand or by the detecting head 1*a* when the same is turnable. When there is no rotational position correcting mechanism, the rotational position of the work is corrected by an electrical procedure or by software. Since the Θ-stage, the work handling mechanism and the detecting head need not be provided with any rotational position correcting mechanism when the rotational position of the work is corrected by an electrical procedure or software, the mechanism can be simplified and miniaturized, and works (wafers) of different sizes can be easily processed.

The rotational position of a work is detected by a method comprising the following steps.

(1) A step of detecting the orientation of the orientation flat of the work (2) A step of detecting the orientation of a pattern formed on the work
① Detection of diffracted light
② Detection of circuit pattern image Feature Extraction More strictly, since the orientation of the circuit pattern and that of the orientation flat are different from each other, the orientation of the circuit pattern must be detected when the orientation of the circuit pattern must be correctly detected.

The rotational position of the work 4 is detected when the wafer 4 moves through a position under the work rotational position detector 110 or is stopped temporarily at a position under the work rotational position detector 110.

The rotational position of the work 4 can be detected through the detection of the orientation flat, a scribe area, chips or a special mark, such as an alignment mark.

A method of adjusting the rotational position of the work 4 will be described below.

Basically, the present invention is intended to be applied to inspecting semiconductor wafers. However, the present invention is applicable to inspecting a work having a substrate and circuit patterns and the like formed on the substrate, such as a liquid crystal display element, and a substrate on which the components of a liquid crystal display element are formed.

An adjacent chip comparing technique is an important technical feature of a dust particle detecting apparatus of the present invention. The adjacent chip comparing technique compares the respective levels of detection signals provided when corresponding points on adjacent chips are detected, and decides that any faults and any dust particles are not found in the adjacent chips when the detection signals are on the same level and that some faults or some dust particles are found on the chip for which the level of the detection signal is higher when the respective levels of the detection signals are greatly different from each other.

The corresponding points on the adjacent chips must be found to use this adjacent chip comparing technique. The corresponding points on the adjacent chips may be found by any suitable method. For example, after obtaining all the data, a correlation function of the data with respect to the x-direction and the y-direction in which the chips are arranged is produced, and the size p of the chips and the direction θ of arrangement may be calculated by using the period of the correlation function. This method needs a storage device of a large capacity for storing the data. Another method uses a design pitch p of the chips and detects the direction in which chips are arranged for each wafer to find corresponding points on the adjacent chips (FIG. 14).

This method needs to find out the direction in which the chips are arranged, i.e., the rotational direction of the wafer. The rotational direction of the wafer may be determined by measuring the orientation of the orientation flat of a wafer 4, provided that patterns are formed on the wafer 4 with reference to the orientation of the orientation flat. Another method measures the direction θ of chips formed on a wafer. However, since most patterns formed on a wafer are complicated, it is difficult to determine the direction of the pattern on the basis of the morphology of the patterns. As shown in FIG. 13, a work rotational position detector 110e projects a light beam on a pattern, and detects a diffraction pattern formed by the diffraction of the light beam by the pattern. Since most patterns formed on wafers are those formed by repeating a basic pattern having an x- and a y-direction, light waves forming a diffraction pattern travel principally in the x- and the y-direction; that is, the zero-order diffracted light 184 travels in the x- and the y-direction as shown in FIG. 13. Therefore, the rotational position θ of the pattern formed on a work 4 can be accurately known by measuring the direction of the zero-order diffracted light from a detected image (diffraction image) 185. This method is able to detect the arrangement of chips on a work (wafer) not provided with any orientation flat or a notch. Since this method measures the pattern formed on the work (wafer) directly, this method is able to achieve measurement and finding corresponding points more accurately than the method that uses the orientation flat or the like.

Figure 13:
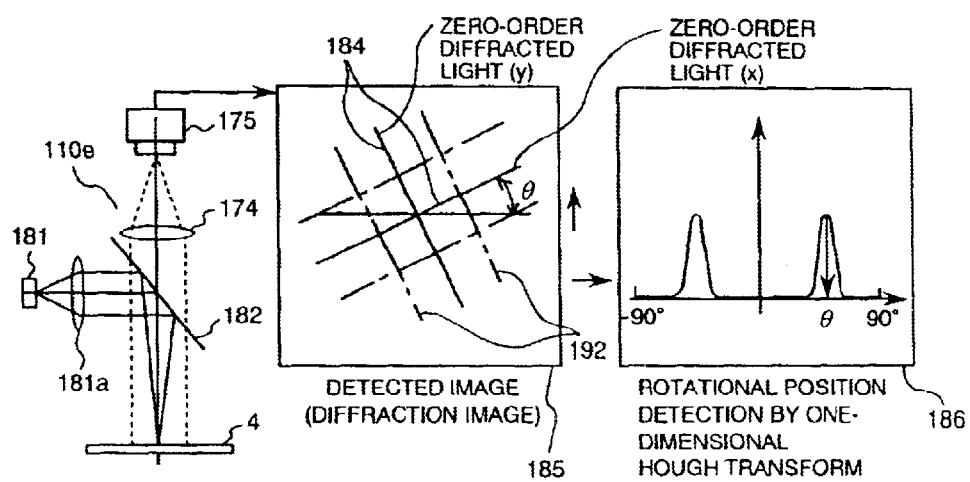
FIG. 13 is a diagrammatic view for assistance in explaining a method of detecting the rotational position of a wafer from a detected image in accordance with the present invention.

The measured direction θ of arrangement of the chips is used for finding the corresponding points of the adjacent chips on the acquired data (the relation 187 between a and a' in FIG. 15), i.e., for correcting the rotational position θ of the chips relative to the pitch p of the chips by an rotational position correcting operator in wafer rotational position correction 187 by an electrical procedure shown in FIG. 13. Image data (image shown in a memory range) provided by a linear image sensor 40 are stored sequentially in a storage 189, a comparing means 190 compares the corresponding points a and a' sequentially for comparative inspection (inspection for faults, such as dust particles). Although this method needs the storage 189 having a storage capacity to store the image data, any mechanism is not necessary and suitable for a highly reliable system.

Another method turns the detecting optical system 36 on the basis of a rotational amount obtained by rotational position detection so that the longitudinal direction in which sensing elements of the linear image sensor (linear detector) 40 are arranged is aligned with the direction θ of arrangement of the chips to position the corresponding points on the adjacent chips are detected by the linear image sensor. Although this method reduces the capacity of the storage 189 necessary for temporarily storing the image data, a rotating mechanism is necessary to turn the detecting optical system 36.

The construction of the work rotational position detector 110e will be described more concretely with reference to FIG. 13. The work rotational position detector 110e comprises a light source 181, which is as similar to a point light source as possible, a half mirror 182, an image forming optical system 174 and a two-dimensional detector 175. Light emitted by the light source 181 travels through the half mirror 182, the image forming optical system 174 and a work 4, and an image of the light source 181 is formed on the detector 175. Basically, the work (wafer) 4 may be considered as a mirror.

Preferably, a telecentric optical system is formed between the image forming optical system 174 and the work (wafer) 4. When a telecentric optical system is formed, the results of detection are not affected significantly by the slight variation of the position of the work 4 with respect to the direction of the optical axis.

FIG. 13 shows an image (diffraction image) detected by the detector 175. The zero-order diffracted light 184 in the x- and the y-direction diffracted by patterns of most semiconductor circuits and display patterns of most liquid crystal displays forms straight lines perpendicular to each other as shown in FIG. 13. The direction of the diffracted light 184 corresponds to the direction θ of arrangement of chips on the work 4. The directions of the straight lines perpendicular to each other can be determined by the well-known Hough transform 186 of the detected image 185. When the work (wafer) 4 is disposed with its surface perpendicular or substantially perpendicular to the optical axis, two-dimensional Hough transform can be compressed in one dimension. The two straight lines are expressed by expressions:

$$x \cdot \sin \theta_1 - y \cdot \cos \theta_1 = 0 \quad (1)$$

$$x \cdot \cos \theta_2 + y \cdot \sin \theta_2 = 0 \quad (2)$$

where $$\theta_2 = (\pi/2) + \theta_1$$

Practically, the number of variables is one because the rotational positions $\theta_1$ and $\theta_2$ of the straight lines are perpendicular to each other. Supposing that the origin of the image is on the optical axis, θ can be calculated by substituting the coordinates of points on the straight lines into Expressions (1) and (2). The angles θ for all the points on the straight lines are calculated, the angles θ are weighted by detection outputs corresponding to the points in the image, and a histogram of the weighted angles is produced. The peaks in the histogram are the $\theta_1$ and $\theta_2$ of the straight lines because signals representing pixels on the straight lines are high.

Practically, the intervals of the histogram into which the range of observed values is divided must be reduced to improve the accuracy of the angle θ. However, when the intervals are reduced, the height of rectangles of the histogram is reduced, a curve connecting the upper ends of the rectangles becomes irregular and the accuracy of calculation of peaks is lowered. A method of calculating barycenter using Expression (3) is suitable for compromising such contradictory conditions. Expression (3) is used for calculating the rotational positions $\theta_1$ and $\theta_2$ can be calculated by a similar expression.

$$\theta_1 = \frac{\sum_{\theta_1-\delta_0<\theta<\theta_1+\delta_0} I(x, y) \cdot \theta(x, y)}{\sum_{\theta_1-\delta_0<\theta<\theta_1+\delta_0} I(x, y)} \quad (3)$$

where I(x, y) expresses, for example, the intensity of the zero-order diffracted light 184 of the detected image 185 shown in FIG. 13.

To carry out this method, the range $\theta_1-\delta_0<\theta<\theta_1+\delta_0$ or $\theta_2-\delta_0<\theta<\theta_2+\delta_0$ including the rotational positions $\theta_1$ and $\theta_2$ must be known. The accuracy of detection is high when the range can be accurately estimated. Therefore, the orientation of the work (wafer), i.e., the direction θ of arrangement of the chips must be adjusted to a value in a certain range by using the orientation flat of the work. Theoretically, perfect values can be calculated even if the range of addition is 0° to 90° when there is no diffracted light of first order and higher orders. Therefore, it is desirable that the intensities of diffracted light of first order and higher are low. Naturally, it is preferable to use two-dimensional Hough transform if the time necessary for calculation does not matter.

Although the histogram is produced by calculating θ, a histogram of tan θ, sin θ or cos θ may be used to save time necessary for calculation.

If the optical axis deviates slightly, calculated θ may possibly includes errors. When the method using the diffracted light is employed, the slight deviation of the optical axis causes the split of peaks of the histogram, which is due to the deviation of the calculated angle including errors to the positive side and the negative side from the true direction θ of the straight line in the case of the diffraction pattern 184. Therefore, when calculating the barycenter, the deviation of the optical axis is cancelled. Accordingly, the method of determining the barycenter by using Expression (3) is able to achieve accurate calculation.

The method using one-dimensional Hough transform can be used also when the center of the optical axis is not on the detected image. More concretely, the image and the center of the optical axis outside the image may be expressed by the same coordinate system.

In the method using the diffracted light, in most cases, a detection signal provided upon the detection of the center of the optical axis is extremely high and the outputs of the detector corresponding to a wide range around the center of the optical axis on the image are saturated. Therefore, in most cases, accuracy of detection is improved when an appropriate range around the center of the optical axis is covered with a mask and are not used for calculating θ. The mask may be a shading plate disposed in the optical system or may be a mask of software.

Practically, as is obvious from the detected image 185 shown in FIG. 13, diffraction patterns 192 of ±first order or ±second order is formed and detected. However, these patterns 192 can be neglected by a method that binarizes the data by using a threshold or a method that uses many-valued data, because the intensity of the patterns 192 is far lower than that of the zero-order diffracted light 184. Although a case using a two-dimensional detector has been described, a rotational position detecting system can be formed by using a one-dimensional detector.

Figure 15:
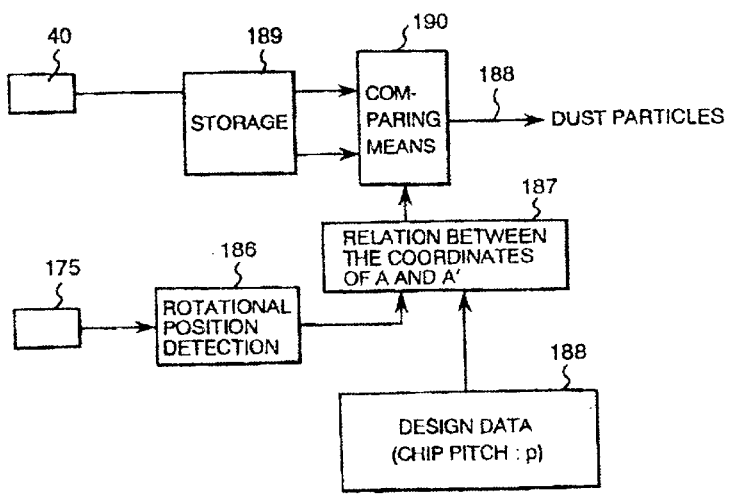
FIG. 15 is a block diagram of a chip comparing system for executing software in accordance with the present invention.

A processing apparatus shown in FIG. 15 is able to correct the deviation of the rotational position of a work. This processing apparatus (correcting apparatus) comprises a rotational position detecting optical system 110e (detector 175), a rotational position calculating system 186, an adjacent chip corresponding point vector calculating system (the coordinate relation between a and a' ) 187, image data storage 189 and a comparing means 190. The rotational position calculating system 186 calculates the direction θ of arrangement of chips by the aforesaid method. An adjacent chip corresponding point vector is calculated by using the direction θ and data on design chip pitch p. The comparing means 190 takes out corresponding points (a and a') by an adjacent chip corresponding point vector with respect to the longitudinal direction of the linear image sensor 40 from the image data storage 189 and compares signal outputs, and a dust particle signal 188 by disagreement is detected. The field of view must be greater than twice the chip pitch. When an allowable inclination for the work (wafer) (an allowable range of inclination of the work for dust particle detection) is θ, the range 1 of memory stored in the image data storage 189 needs a capacity for recording the range of length equal to the product of the size of the field of view and sin θ.

Correction of the rotational position by a work scanning direction comparing system will be described hereinafter. In the foregoing description, the adjacent chips to be compared are arranged in the longitudinal direction of the linear image sensor 40. The adjacent chips to be compared need not necessarily be arranged in the longitudinal direction of the linear image sensor 40 and may be arranged in the work scanning direction perpendicular to the longitudinal direction of the linear image sensor 40. The corresponding points on the adjacent chips can be determined by calculating an adjacent chip corresponding point vector for the adjacent chips arranged in a direction perpendicular to the longitudinal direction of the linear image sensor 40. The size (memory range 1) of the storage can be calculated by a similar operation.

In this case, the chips can be compared even if the detection field of view is not far greater than the chip size. On the other hand, the corresponding points on the adjacent chips arranged in the scanning direction must be accurately known by accurately feeding the work by a handling mechanism or the like. This scanning direction comparison is affected scarcely by irregular illumination and irregularities in the detection lens when θ is nearly zero.

Rotational position correction by a rotational position adjusting mechanism will be described hereinafter. The calculation of the corresponding points on the adjacent chips can be simplified by turning the optical system 36 (illuminating system 31 and the rotational position detecting optical system 110 may be turned together with the optical system 36) on the basis of the direction θ of arrangement of the chips calculated by the rotational position calculating system 186. The chip comparing means 191 takes out the corresponding point from the information stored in the storage 189, the signal outputs are compared and a dust particle signal 188 by disagreement is detected. This method is effective even if the accuracy (irregular feed speed, vibrations along the optical axis and vibrations in the scanning direction) of the scanning mechanism for scanning the work is not very high. When this rotational position adjusting mechanism is used, the scanning direction and the direction of arrangement of the chips need not be perpendicular to each other. When the spatial filter 39 is used, the angle of the spatial filter 39 corresponds accurately to the arrangement of the chips and hence it is possible to make the most of the effect of the spatial filter 39.

Figure 16:
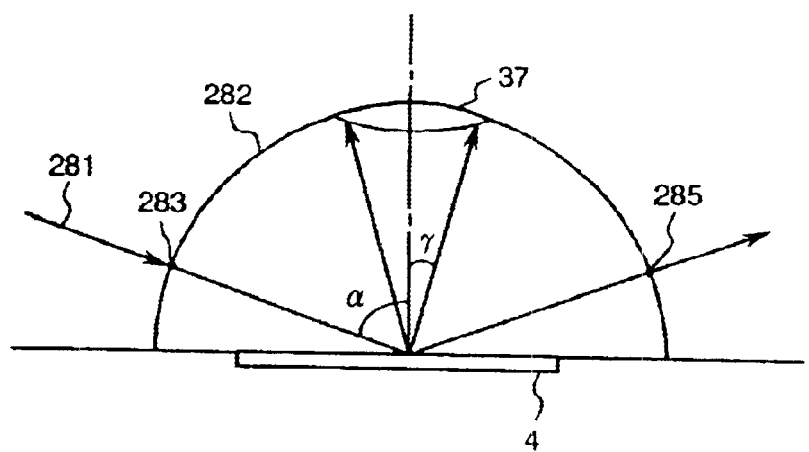
FIG. 16 is a diagrammatic view showing the relation between illuminating light, diffracted light diffracted by a wafer, and the aperture number of an objective.
Figure 17:
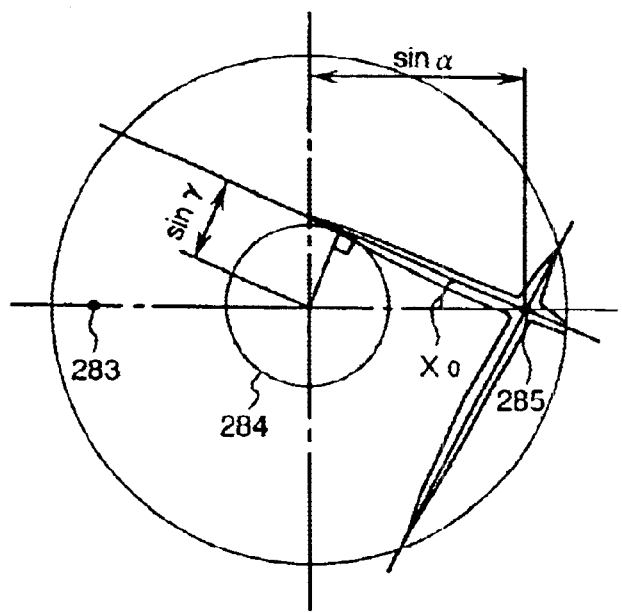
FIG. 17 is a diagrammatic view showing the relation between illuminating light, diffracted light diffracted by a wafer, and the aperture number of an objective.
Figure 18:
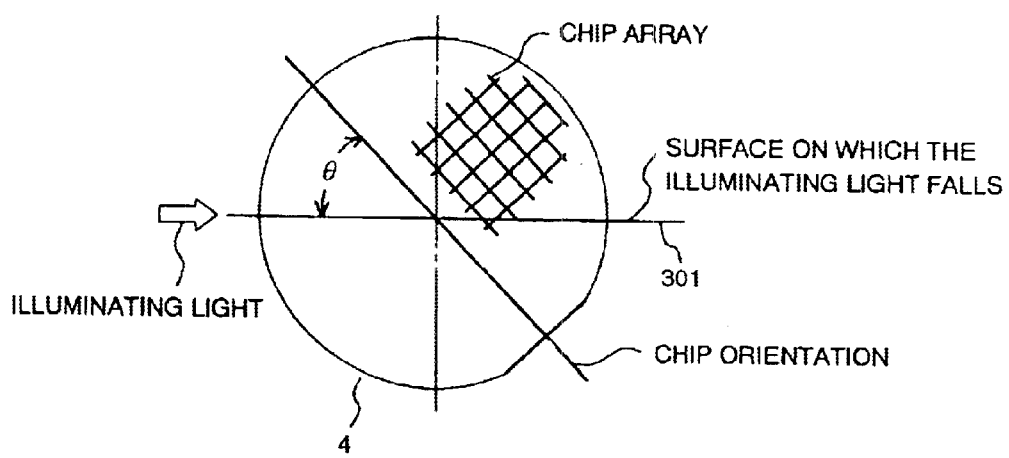
FIG. 18 is a diagrammatic view showing the direction of arrangement of chips on a wafer.

Zero-order cut spatial filter system+chip comparison will be described hereinafter. When the chip comparing system is used, the spatial filter 39 for filtering nth-order diffracted light need not necessarily be used. Particularly, when the minimum cell size of a chip pattern formed on the work 4 is small and diffracted light of first order and higher does not fall on the detection lens 37, only zero-order diffracted light needs to be intercepted. In such a case, measures to be taken to cope with the warp of the work and the inclination of the work 4 when the spatial filter 39 is used are unnecessary. FIGS. 16 and 17 show the diffracted light and the condition of the aperture of the detection lens when the direction of arrangement of the chips on the work is θ as shown in FIG. 18. Shown in FIGS. 16 and 17 are the incident angle ≠ of the illuminating light, the radial angle γ of the detection lens 37, a spherical surface 282, the intersection point 283 of the illuminating light and the spherical surface 282, and the intersection line 284 of the spherical surface 282 and the radial angle of the detection lens 37. The illuminating light 281 falls on the spherical surface 282 at the inter-section point 283 and the reflected illuminating light leaves the spherical surface 282 at a leaving point 285. Information about principal patterns on the work 4 can be erased by turning the work 4 in the direction θ so that zero-order diffracted light may not fall on the detection lens 37, whereby dust particles on the patterns on the work 4 or faults in the patterns can be emphasized for detection. The dust particles and the faults can be detected by executing chip comparison after detection. The work 4 is turned to x0 (Expression (4)) to move the detecting optical system 38 away from the patterns; that is the work 4 is turned through x0–θ relative to the detecting optical system 38.

$$\sin \alpha \cdot \sin(x0) > \sin \gamma \qquad (4)$$

The maximum value $x0_{(max)}$ is obtained from Expression (4) by using the following expression.

$$\sin(x0_{(max)}) = \sin \gamma / \sin \alpha \qquad (5)$$

The rotational stroke of the work 4 relative to the detecting optical system 36 including the detector 40 is selected to realize $x0_{(max)}$. More concretely, when the NA=sin γ of the objective 37 of the detecting optical system 36 is on the order of 0.1 (focal length f=about 70 mm (FIG. 10(b), the focal length f must be about 50 mm or above to detect dust particles on the work 4 through the transparent window 106 from outside the transfer chamber 104), the depth of focus is about ±60 μm (the depth of focus must be ±40 μm to ±30 μm to detect dust particles on the work (wafer) 4 without automatic focusing) and α=60°, $x0_{(max)}$ is about 6.6°. When the NA=sin γ of the objective 37 of the detecting optical system 36 is on the order of 0.08 (focal length f=about 90 mm, depth of focus is about ±60 μm) and α=85°, $x0_{(max)}$ is about 4.6°. Rotational strokes, i.e., $x0_{(max)}$, in the range of 5° to about 10° is a satisfactory allowable rotation range. When the work (wafer) 4 is transported in the angle θ meeting θ>$x0_{(max)}$, the work 4 or the detecting optical system 36 need not be turned.

Figure 19:
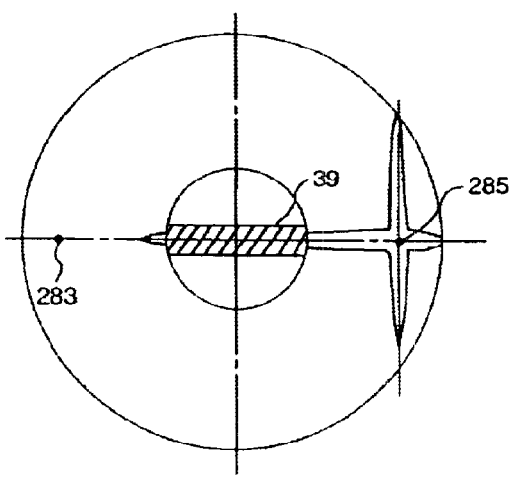
FIG. 19 is a diagrammatic view for assistance in explaining the interception of zero-order diffracted light by a spatial filter.

The foregoing method does not need the zero-order cut filter 39 in the detecting optical system 36 and hence the image forming performance of the detecting optical system is not deteriorated. Since it is satisfactory only if zero-order diffracted light is intercepted, the setting may be made so that the angle θ of the work 4 is 0°. In such a case, a zero-order cut filter 39 shown in FIGS. 3 and 19 is necessary. The width of the cut filter 39 is determined empirically so that the zero-order cut filter 39 is able to intercept zero-order diffracted light satisfactorily. As mentioned above, the method that detects the rotational position of the work 4, corrects the rotational position, calculates the chip arrangement vector and carries out chip comparison, and a method that does not detect the rotational position of the work 4 and does not carry out chip comparison are possible. The detection sensitivity of the method that carries out chip comparison is lower than that of the method that does not carry out chip comparison. Particularly, since the patterns formed on the work 4 have various directional components, such as rounded corners, the zero-order cut filter 39 is unable to intercept zero-order diffracted light perfectly. Therefore part of zero-order diffracted light that cannot be intercepted by the zero-order cut filter 39 is removed through chip comparison.

Installation of the detecting unit (detecting head 1a, the work handling mechanism 5 and such) will be described. The detecting unit may be installed in a predetermined manner in the processing apparatus (FIGS. 1, 9 and 10), the work handling mechanism 5 (FIGS. 1, 9 and 10), and the wafer stocker, not shown. When inspecting the work 4, the work 4 is moved so that the surface to be inspected of the work 4 pass through a range corresponding to the depth of focus of the detecting optical system 36 included in the detecting unit (detecting head 1a). In some cases, the stage supporting the work 4 or the work handling mechanism 5 is unable to absorb the warp of the work 4. In such a case, automatic focusing or automatic inclination adjustment is necessary. However, the curvature of the warp of the work 4 is on a level which does not matter.

The arm 5a of the work handling mechanism 5 for transporting the work (wafer) 4 will be described hereinafter. The work 4 needs to be moved so that the surface to be inspected of the work 4 pass through the range of the depth of focus of the detecting optical system 36 of the detecting unit (detecting head 1a). Since vacuum chucking is impossible in a vacuum, an electrostatic chucking system is desirable. The warp of the work 4 must be within about ±10 μm.

The stage is used as the arm 5a of the work handling mechanism 5 and is intended to remove the warp of the work 4. Naturally, the arm 5a is used not only for dust particle detection, but also for other purposes in which the warp of the work 4 matters. The arm 5a of the work handling mechanism (work handling robot) 5 is installed in the processing apparatus (FIGS. 1, 9 and 10), the work handling mechanism 5 (FIGS. 1, 9 and 10) and the work stocker, not shown, to transport the work 4.

Figure 20A:
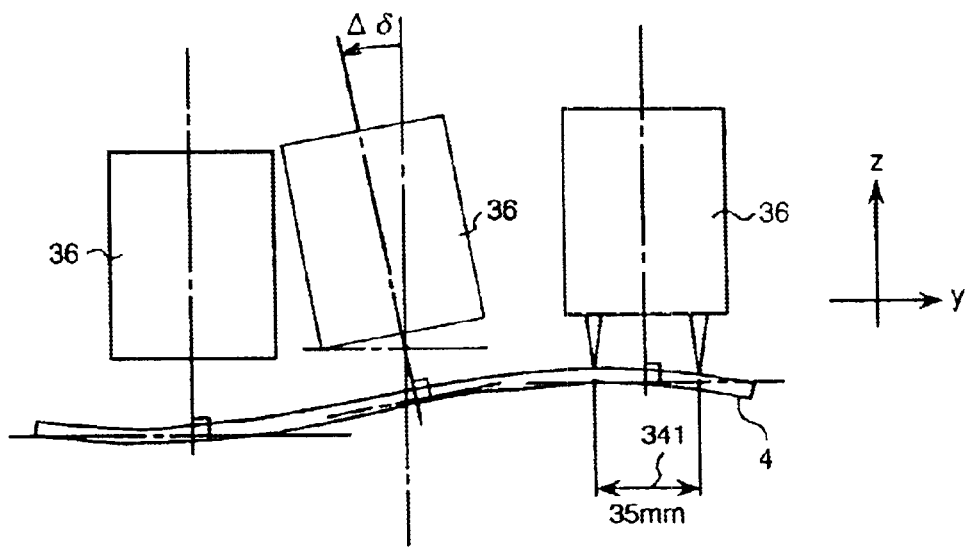
FIG. 20(a) is a front view of an inclination detecting optical system for detecting the inclination of a waver on the basis of a warp of the wafer.
Figure 20B:
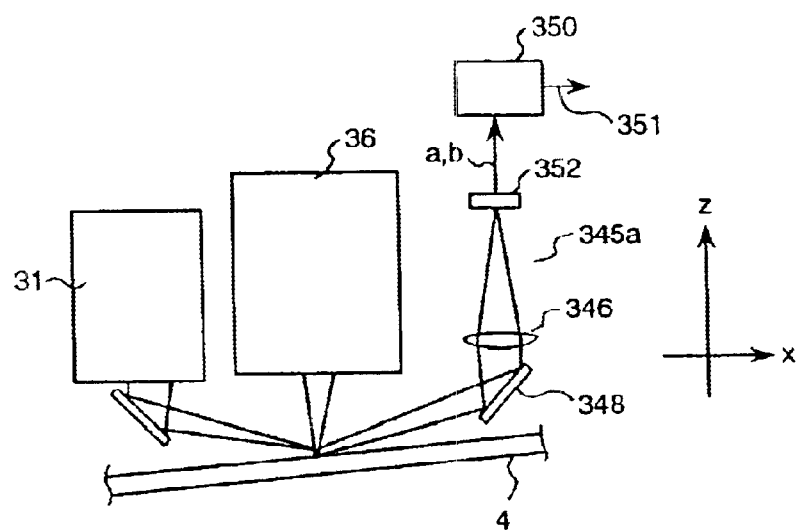
FIG. 20(b) is a side view of the inclination detecting optical system of FIG. 20(a)
Figure 21A:
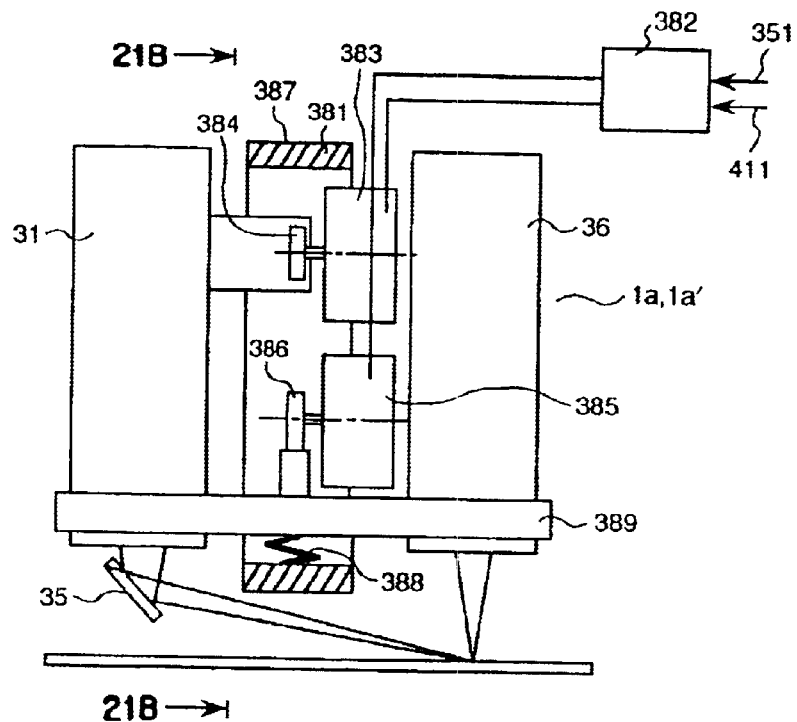
FIG. 21(a) is a schematic front view of a mechanism for the adjustment of the inclination and the automatic focusing of a detecting unit (detecting head)
Figure 21B:
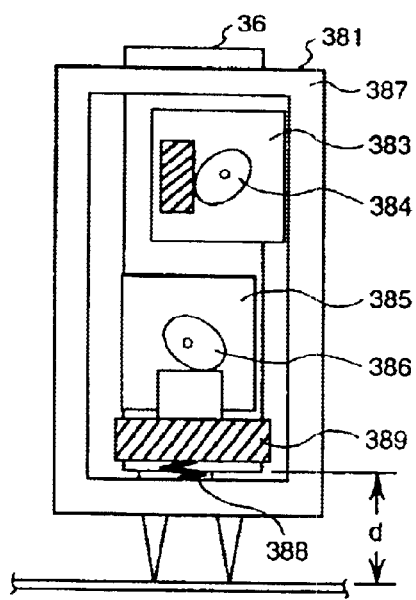
FIG. 21(b) is a sectional view taken on line 21B—21B in FIG. 21(a)

An apparatus for removing the warp of the work 4 will be described with reference to FIGS. 20 and 21. The following two problems arise in the dust particle detecting apparatus 1 of the present invention when the work 4 is warped. When the work 4 is warped, the position of the focus of the detecting optical system 36 (the objective 37) changes. For example, when the 8 in. diameter work 4 is warped so that the central portion thereof is convex upward by 400 μm relative to the periphery thereof as shown in FIG. 20(a), the maximum height variation, i.e., variation along the optical axis, of a portion of the surface of the work 4 in the field of view 341 of 35 mm is about 140 μm When the work 4 is warped, the surface is inclined and the position of the Fourier transform image of the patterns on the work 4 is dislocated from a correct position relative to the spatial filter 39, whereby the spatial filter ring effect is spoiled. When the inclination Δδ=140 μm/35 mm (f (focal length of the detecting optical system 36 (objective 37))=70 mm), the positional dislocation on the Fourier transform plane (the position of the spatial filter 39) is 280 μm.

The following method is necessary to solve those two problems.

As mentioned above, even if the work 4 is warped in a complex shape, it is considered that a portion of the surface of the work in the field of view 341 of 35 mm is substantially flat. Accordingly, the dust particle detecting apparatus may be provided with an optical axis adjusting mechanism as shown in FIG. 21 to align the optical axis with a normal to the center of the field of view 341. As shown in FIG. 21, the optical axis adjusting mechanism comprises a light source 31, an image forming optical system 346 provided with a mirror 348, a two-division detector 352 (one-dimensional or two-dimensional image sensor may be used), a signal processing system 350 for processing signals a and b provided by the two-division detector 352, a driving unit 383, and a controller 382 that receives a signal 351 indicating the inclination $\Delta\delta$ of the surface of the work 4 provided by the signal processing system 350 and controls the driving unit 383. Light emitted by the light source 31 is reflected by the surface of the work 4 and an image of the surface of the work 4 is formed on the two-division detector 352 by the image forming optical system 346. The signal processing system 350 processes the signal a provided by the light receiving unit 352a and a signal b provided by the two-division detector 352 to calculate, for example, contrast by using (a−b)/(a+b), an optical axis adjusting mechanism 381 turns the detecting optical system 36 in a plane including the optical axis and the linear detector 40 in the direction of the arrow (FIG. 20(a)) through an angle $\Delta\delta$ so that (a−b)/(a+B)=0, i.e., so that the optical axis is aligned with the normal. This optical axis adjusting operation is continued automatically while the detecting optical system 36 scans the work 4. The two-division detector 352 receives a light beam 354 indicated by continuous line aligned with the center axis 356 when the surface of the work 4 is not inclined, and receives a light beam 355 indicated by dotted line deviating from the center axis 356 when the surface of the work is inclined in the direction of $\Delta\delta$.

The signal processing system 350 may calculate the difference a−b or the ratio a/b instead of the contrast. desirably, the detecting optical system 36 is turned about the intersection of the optical axis and the work 4 or a point near the intersection because the field of view on the work 4 does not change in a direction perpendicular to the scanning direction when the detecting optical system 36 is turned about the intersection.

The construction of the optical axis adjusting mechanism 381 may be of a construction using ball bearings, plate springs, coil springs or linkages. FIG. 21 shows the optical axis adjusting mechanism 381 employing a coil spring 388 by way of example. The center of turning for adjusting the optical axis is near the center of the coil spring 388 and is separated slightly from the intersection of the optical axis and the work 4. However, the center of turning is considered to be satisfactorily close to the intersection, because, when the distance d=35 mm between the center of turning and the intersection, the surface of the work 4 is inclined in the aforesaid manner and the inclination of the optical axis is adjusted by the aforesaid method, the dislocation of the field of view in the direction toward the detector is (140 μm/35 mm)·(d=35 mm)=140 μm, which is not very large to cause troubles. The center of turning can be moved toward the intersection by using a linkage. The driving system for turning the detecting optical system 36 through the angle $\Delta\delta$ may employ a piezoelectric device or may employ a stepping motor 383 and a cam mechanism 384 mounted on the output shaft of the stepping motor 383 as shown in FIG. 21. Indicated at 387 is a base frame holding the detecting head 1a. The stepping motor 383 and a stepping motor 385 are mounted on the base frame 387. The illuminating optical system 31 and the detecting optical system 36 are attached to a plate 389. The illuminating optical system 31 and the detecting optical system 36 are turned through the angle $\Delta\delta$ on the coil spring 388 by the stepping motor 383 through the cam mechanism 384 for optical axis adjustment. The stepping motor 385 and a cam mechanism 386 move the plate 389 by z in the Z-direction for correction.

The warp detecting system can be used as an automatic focus detecting system. The automatic focus detecting system may use light or electrostatic capacity or may detect a change in pneumatic pressure.

Figure 22A:
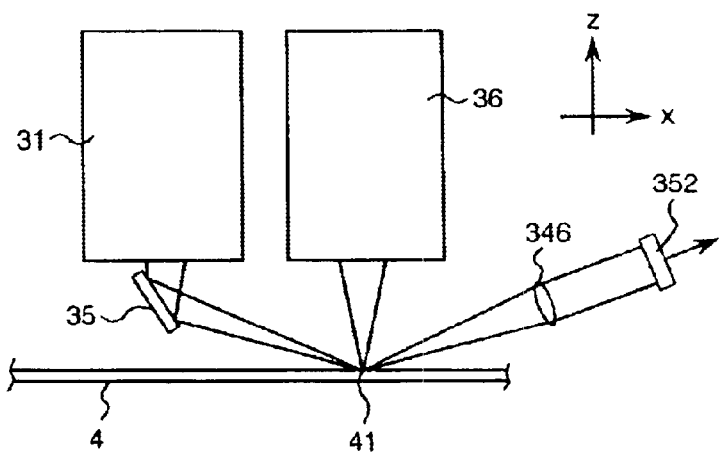
FIGS. 22(a) and 22(b) are front views of optical systems for detecting inclination and focal point by using illuminating light emitted by an illuminating optical system.
Figure 22B:
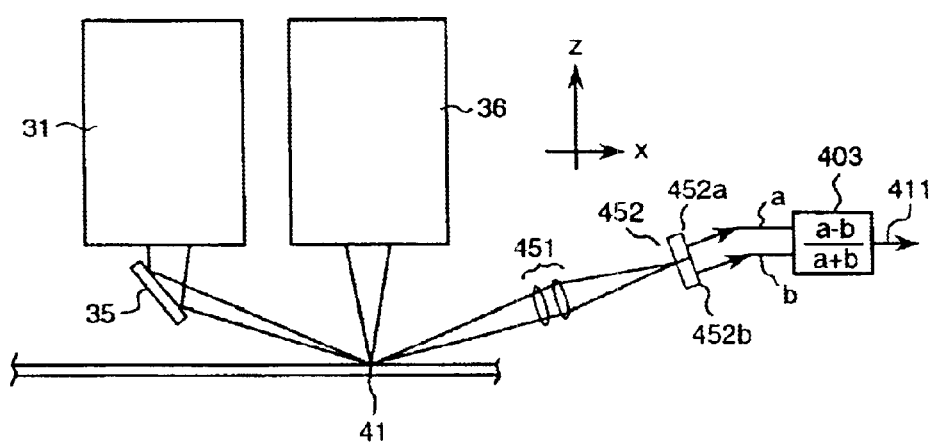
Figure 23:
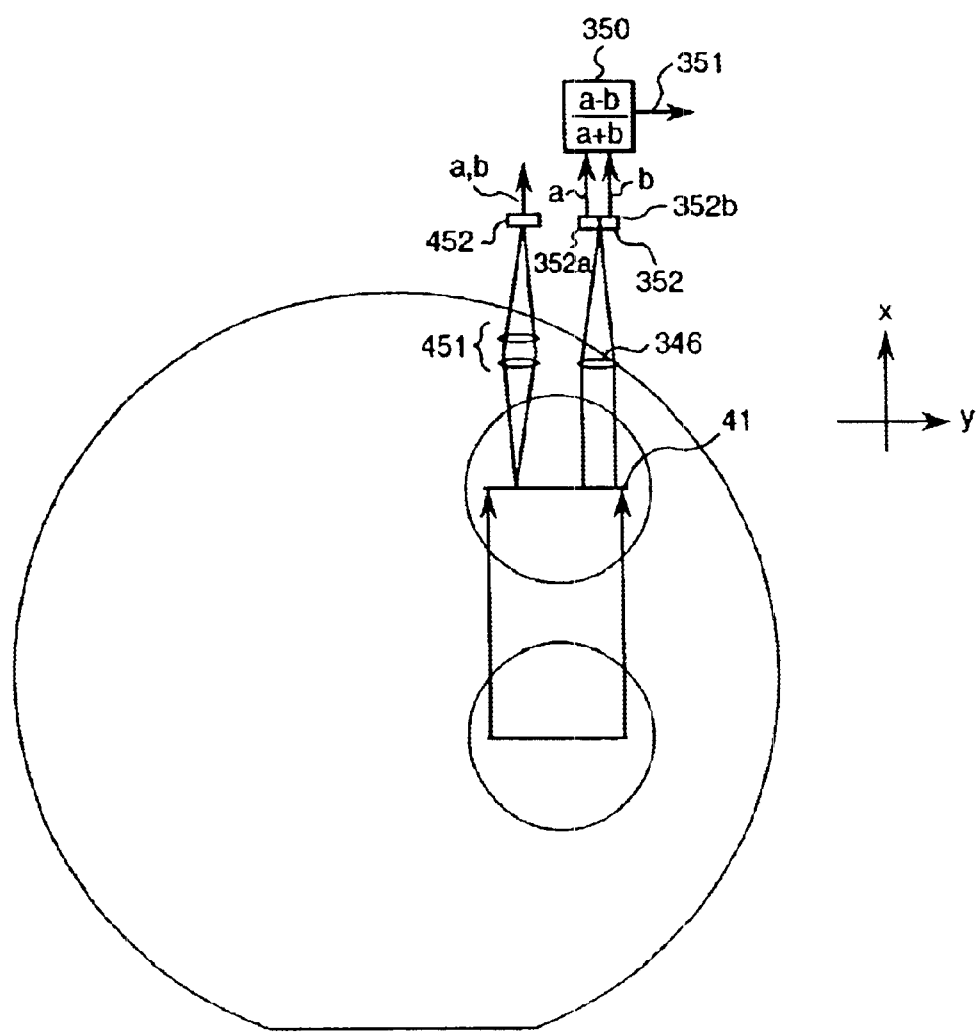
FIG. 23 is a plan view of an optical system for detecting inclination and focal point by using illuminating light emitted by an illuminating optical system.

FIGS. 22 and 23 show an optical axis adjusting and automatic focusing system. An illuminating optical system 21 projects a light beam 41 on the surface of the work 4, and an image forming optical system 451 forms an image on a two-division detector (one-dimensional or two-dimensional image sensor) 452. The automatic focusing of the detecting optical system 36 can be achieved by adjusting the position of the same so that the image of the light beam 41 is formed at the center of the two-division detector 452, i.e., the boundary between the light receiving units 452a and 452b of the two-division detector 452. For example, a signal processing system 403 processes signals a and b respectively provided by the light receiving units 452a and 452b and calculates (a−b)/(a+b), and the detecting optical system 36 can be automatically focused on the surface of the work 4 by minutely moving the same in the Z-direction as shown in FIG. 21 so that (a−b)/(a+b)=0. At the same time, the light beam 41 projected on the surface of the work 4 by the illuminating system 31 is focused on the two-division detector (one-dimensional or two-dimensional image sensor) 352 by the image forming optical system 346, and the optical axis of the detecting optical system 36 can be aligned with the normal to the inclined surface of the work 4 by adjusting the inclination of the detecting optical system so that the image of the light beam 41 is formed at the center of the two-division detector 352, i.e., the boundary between the light receiving units 352a and 352b. For example, a signal processing system 350 processes signals a and b respectively provided by the light receiving units 352a and 352b and calculates (a−b)/(a+b), and the optical axis of the detecting optical system 36 can be aligned with the normal to the inclined surface of the work 4 by minutely turning the same through the angle as shown in FIG. 20 so that (a−b)/(a+b)=0. The optical axis adjusting and automatic focusing system shown in FIGS. 22 and 23 employs the two-division detectors 352 and 452, and uses the illuminating optical system 31 to be used for inspection. When detecting the inclination of the work 4, the two-division detector 352 is disposed so as to be divided into the two units with respect to the y-direction at the Fourier transform position of the illuminated point on the work 4. For automatic focusing, the two-division detector 452 is disposed so as to be divided into the two units with respect to the x-direction at a position where the illuminated point on the work is formed. This arrangement does not need any additional illuminating system.

A method of installing the detecting unit (detecting head 1a (1a')) in a processing apparatus (a sputtering apparatus for forming a metal thin film, such as an Al thin film, on the work 4, a CVD apparatus for forming an insulating film on the work 4, an etching apparatus for etching (FIGS. 1, 9 and 10) or a work stocker, not shown, will be described with reference to FIG. 24.

Figure 14:
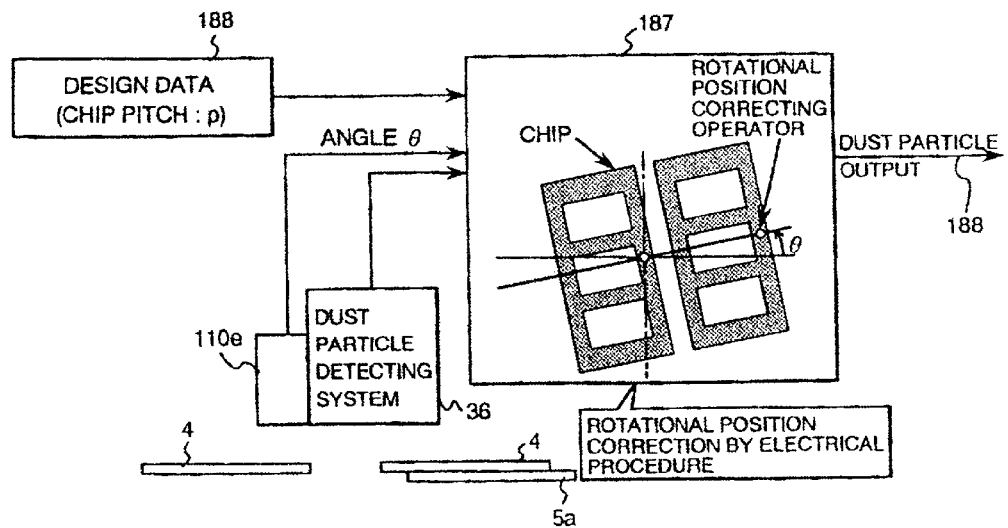
FIG. 14 is a diagrammatic view for assistance in explaining rotational position correcting operation in comparing chips in accordance with the present invention.

When comparing two chips, an rotational position correcting operator 187 as shown in FIGS. 14 and 15 is necessary. The rotational position correcting operator 187 can be substituted by a software procedure (electrical procedure). However, when the spatial filter 39 (zero-order cut filter) is employed (FIGS. 3 and 19), the direction of the spatial filter 39 must be aligned with the direction θ of the chip array formed on the work 4. When the spatial filter 39 is not used (FIG. 17), the direction θ of the chip array formed on the work 4 must be greater than $x0_{(max)}$. When the work 4 is transported by the arm 5a of the work handling mechanism 5 through the processing apparatus, the orientation of the work 4 is determined by using the orientation flat and the deviation of the rotational position of the work 4 from a correct rotational position is within ±10°. Therefore, the position of either the work 4 or the detecting unit (detecting head 1a (1a')) must be adjusted for correcting the deviation of the rotational position of the work 4.

When adjusting the rotational position of the work 4 relative to the detecting unit (detecting head 1a (1a')) by moving the work 4, the work 4 needs to be turned minutely on the extremity (the center of the work 4) of the arm 5a of the work handling mechanism 5, which requires complex control operations for driving the arm 5a. The rotational position can be corrected by minutely turning a rotary stage mounted on the extremity of the arm 5a, which makes the mechanism of the arm complex. A rotary stage separate from the arm 5a may be used, which requires additional space for installing the rotary stage. Thus, the work handling mechanism 5 must be of a special type to be installed in the processing apparatus and a general-purpose handling mechanism cannot be used.

Those problems can be solved by correcting the deviation of the rotational position by the detecting unit (detecting head 1a (1a')). However, the detecting unit (detecting head 1a (1a')) needs a somewhat complex mechanism.

Figure 24A:
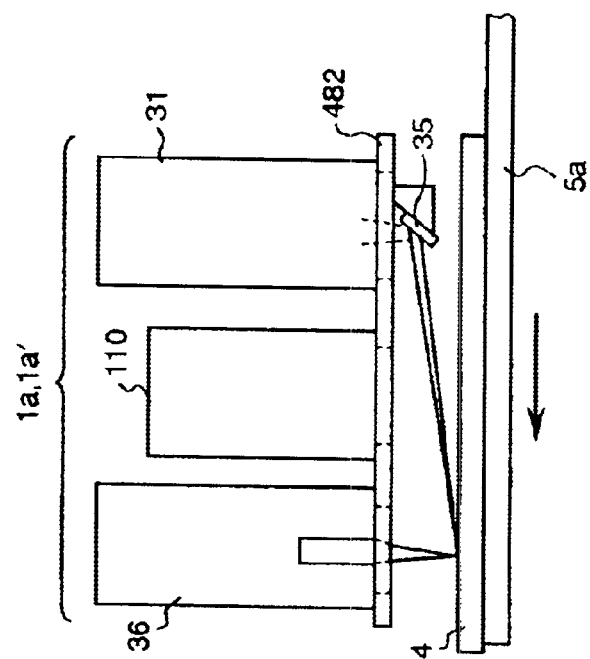
FIGS. 24(a) and 24(b) are front view and a side view, respectively, of a mounting mechanism for simply installing a detecting unit (detecting head)
Figure 24B:
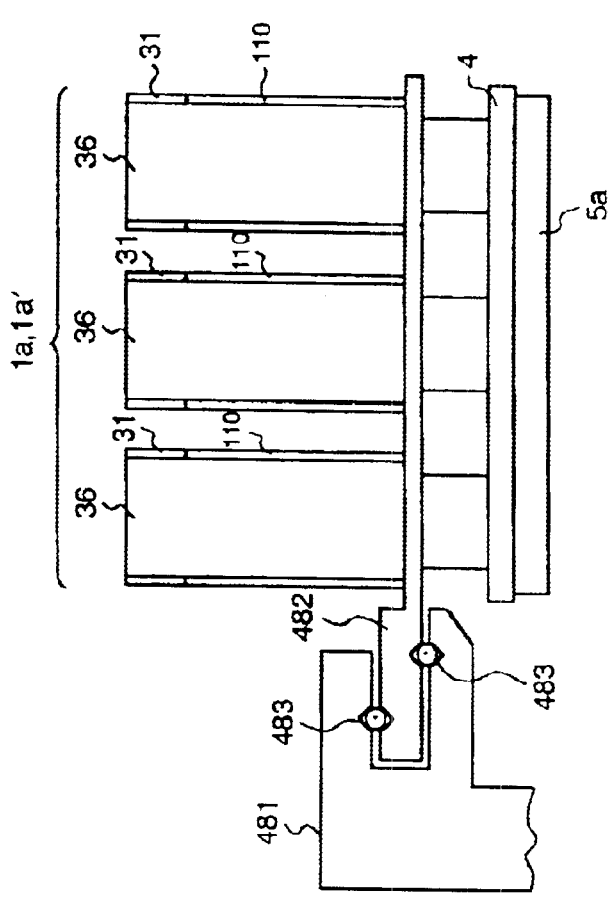

FIG. 24 shows an detecting unit (detecting head 1a (1a')) not provided with any rotational position correcting mechanism and supported in a cantilever fashion. The detecting unit (detecting head 1a (1a')) of, for example, three channels is mounted on a plate 482, and a mirror 35 is attached to the lower surface of the plate 482. The mirror 35 need not necessarily be attached to the plate 482. The plate 482 is supported in a cantilever fashion on a base 481. The detection unit (detecting head 1a (1a')) can be easily removed by a removing mechanism employing steel balls (or rollers) 483. The use of the steel balls (or rollers) 483 eliminates work for readjustment when the detecting unit (detecting head 1a (1a')) is to be mounted again on the base 481.

Figure 25:
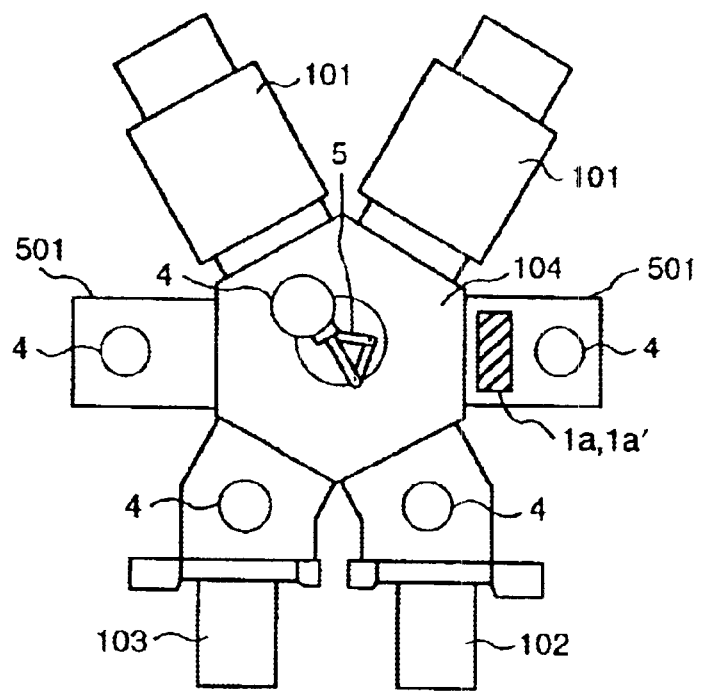
FIG. 25 is a plan view of a processing apparatus in accordance with the present invention provided with a detecting unit in its buffer chamber.

The application of the detecting unit (detecting head 1a (1a')) of the dust particle detecting apparatus 1 similarly to the embodiments shown in FIGS. 1, 9 and 10) to a processing apparatus will be described hereinafter with reference to FIG. 25. The use of wafers of greater diameters for fabricating semiconductor devices has progressively increased to enhance production efficiency. The curtailment of days necessary to complete products has been pressing concern. Single wafer processing has become prevalent in film forming apparatuses and etching apparatuses to cope with the foregoing problems. The stable operation of those processing apparatuses and keeping the days necessary to complete products from increasing are necessary. The present invention is intended to solve those problems by inspecting wafers for dust particles and faults before and after processing the wafers. Concretely, the present invention uses a multichamber system employing a central transfer chamber 104 having at least one partition wall shown in broken section in FIG. 1, the central transfer chamber 104 being; disposed at the center of an arrangement of a plurality of processing apparatuses disposed in respective processing chamber 101 as shown in FIGS. 10 and 25, and the detecting unit (detecting head 1a (1a')) is disposed on the central transfer chamber 104. This arrangement enables the standardization of an interface between the dust particle detecting apparatus 1 and the processing apparatuses and the smooth application of the dust particle detecting apparatus 1.

The detecting unit (detecting head 1a (1a')) may be installed in one of multiple chambers, i.e., a buffer chamber 501 instead of installing the same on the central transfer chamber 104. In some cases, a work is subjected to a plurality of processes in a vacuum in those processing apparatuses without exposing the work to the atmosphere, which requires the inspection of the work for dust particles in a vacuum. Therefore, dust particles on the work disposed in a vacuum chamber is detected through a dummy port, not shown, formed in one of the walls defining the vacuum chamber by the detecting unit (detecting head 1a (1a')) installed in the atmosphere as shown in FIG. 10.

When the detecting unit (detecting head 1a (1a')) is spaced apart from the dummy port and the position of the detecting unit (detecting head 1a (1a')) is adjustable, the positional adjustment of the optical system relative to the arm 5a can be easily accomplished. When installing the removed detecting unit (detecting head 1a (1a')), only the positional adjustment of the optical systems 31 and 36 with respect to the z-direction, and the adjustment of the inclination of the linear field of view of the optical systems 31 and 36 are necessary. When the aforesaid mechanisms for automatic inclination correction according to the warp of the work 4, and automatic focusing are employed, the optical systems 31 and 36 must be spaced apart from the dummy port and the positions of the optical systems 31 and 36 date be adjustable. When the illuminating optical system 31 emits an illuminating light beam of a sufficiently high intensity and a sufficiently large width, automatic focusing and automatic inclination correction can be achieved only by the detecting optical system 36 and hence some parts including the mirror 35 may be disposed near the dummy port. When the detecting system of such a type is used, the detecting unit (detecting head 1a (1a')) can be installed as it is on the processing apparatus not having any vacuum chamber. When the objective of the detecting optical system 36 has a large NA of, for example, 0.2 to 0.3, a problem arises due to aberration by the objective 37. When designing the lens system, the dummy port must be taken into consideration. Therefore, a window like that shown must be used for aberration correction even in the atmosphere.

FIG. 24 shows a mechanism that facilitate removing the detecting unit (detecting head 1a (1a')). This mechanism employs steel balls (or rollers) 483. The use of the steel balls (or rollers) 483 eliminates work for readjustment when the detecting unit (detecting head 1a (1a')) is to be mounted again on the base 481.

It is desirable to project the illuminating light beam on the work 4 at the smallest possible incident angle α near 60° when the film formed on the work 4 consists of grains of comparatively large grain sizes. It is desirable to project the illuminating light beam on the work 4 at the largest possible incident angle α of 80° to 85° when the film formed on the work 4 consists of grains of comparatively small grain sizes and the surface of the film is a substantially mirror-finished surface because the reflection of the illuminating light beam by the grains of the film is suppressed and dust particles are emphasized when the incident angle α is small. A smaller incident angle is desirable when the surface of the film is nearly a mirror-finished surface, to enable the detection of forward scattering. Since the on-machine dust particle detecting apparatus of the present invention is installed on a processing apparatus for forming a film of a known quality, an incident angle suitable for inspecting the film must be chosen.

Figure 26A:
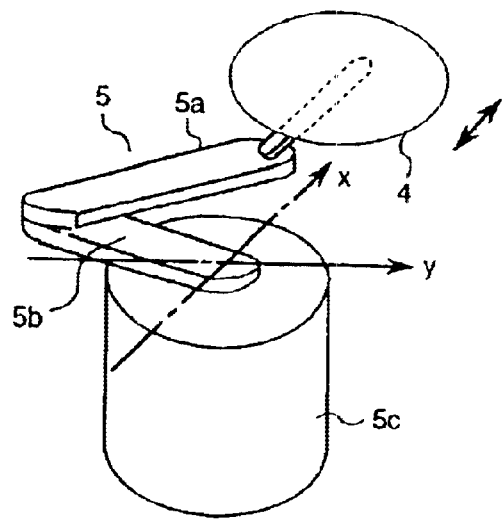
FIGS. 26(a) and 26(b) are perspective view and a diagrammatic view, respectively, for assistance in explaining a method of transporting a work by a work handling mechanism (work handling robot)
Figure 26B:
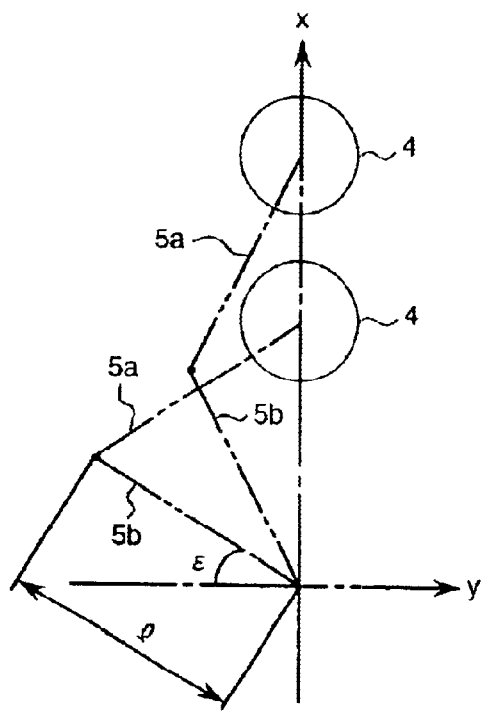

A scanning mode (transfer mode) for dust particle detection will be described hereinafter with reference to FIGS. 26 and 27. FIGS. 26(a) and 26(b) show a general work handling mechanism (work handling robot) 5. The work handling mechanism 5 comprises a shoulder unit 5c, an upper arm unit 5b supported for turning about a vertical axis and driven by a motor, not shown, and a forearm unit 5a supported for turning about a vertical axis on the extremity of the upper arm 5b and driven by a motor, not shown. When the forearm unit 5a is turned at a fixed angular speed, the work 4 is not transported at a constant speed. Therefore, in some cases, the detection output varies due to the variation of pixel size from position to position and a change in the accumulating time, when detecting dust particles by the linear image sensor 40. The variation of the detection output, as mentioned above with reference to FIGS. 14 and 15, causes problems in calculating the corresponding points on the chips for comparison.

Therefore, 1) the work handling mechanism 5 must be controlled so that the work 4 is moved along a straight line, 2) the accumulating time for detection must be controlled so that the image plane may not be distorted and 3) a distorted image is picked up and the corresponding points on the chips are made to correspond to each other when correcting the rotational position of the work 4 by an electric circuit.

When the work handling mechanism 5 of this type is used, the moving speed of the work 4 varies sinusoidally with time and the position of the work 4 varies sinusoidally with time. The position x of the work 4 is expressed by:

$$x = l \cdot \sin(\omega t) \quad (6)$$

where $\omega$ is the angular speed of the axis of rotation of the work handling mechanism 5. Therefore, the scanning speed of the work 4 is the derivative of x with respect to time t.

$$dx/dt = l \cdot \omega \cdot \cos t(\omega t) \quad (7)$$

Figure 27A:
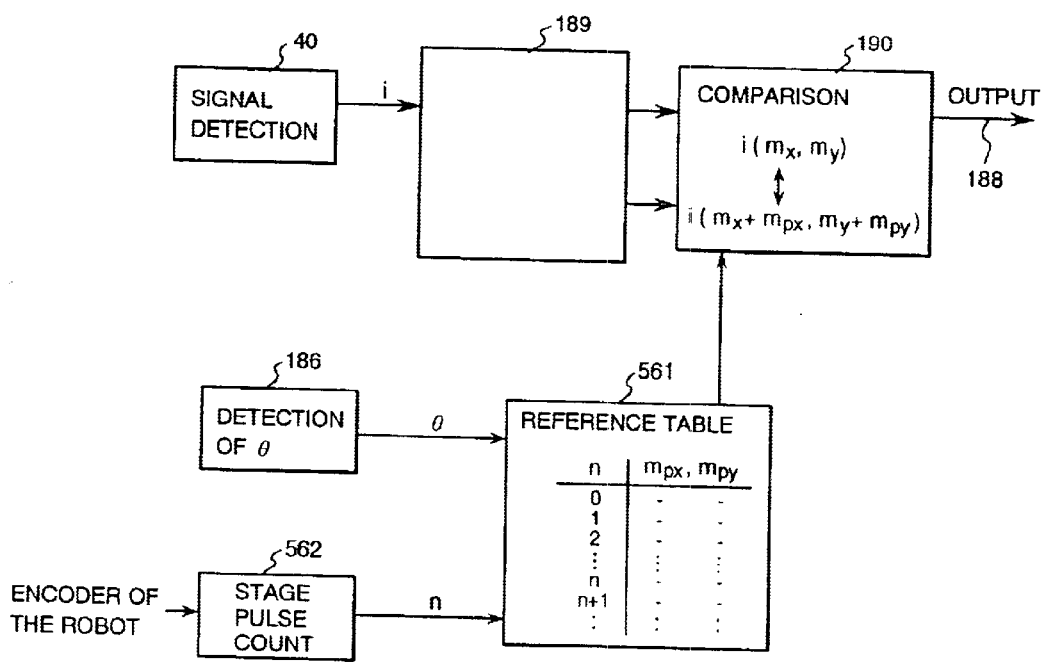
FIG. 27(a) is a block diagram for assistance in explaining chip comparison taking into consideration speed variation when conveying a work by a work handling mechanism (work handling robot) in accordance with the present invention.

A method of making the corresponding points on the chips correspond to each other when correcting the rotational position of the work 4 by the electric circuit will be described with reference to FIG. 27(a). The inclination $\theta$ of the work 4 is calculated in the rotational position detecting process 186 by processing signals provided by the work rotational position detector 110. The coordinate relation (mpx, mpy) between the chips to be compared is determined according to the inclination $\theta$ of the work 4 by using a reference table 561. Information about the chips to be compared is extracted from detection signals stored in the memory 189 and compared by the comparing means 190 according to the coordinate relation (mpx, mpy). The reference table 561 is used to enhance the speed of the arithmetic operations and is not necessarily essential. The work scanning speed dx/dt and the distortion of the detected image are dependent on the positions of the arms 5a and 5b of the work handling mechanism 5. Therefore, the distortion of the detected image is dependent on the speeds of the arms 5a and 5b, and hence the coordinates indicating the positions of the corresponding points on the chips correspond to the positions of the arms 5a and 5b. The correspondence between the coordinates of the corresponding points on the chips and the positions of the arms 5a and 5b is shown in the reference table 561.

Suppose, by way of example, that the length l of the arm of the work handling mechanism 5 is 100 mm, the initial phase $\epsilon 0$ of the arm is 30⁻ (the range of phase of the arm is defined by: $-30° < \epsilon < 30°$), the rotational pulse rate of the work handling mechanism 5 is f0, pixel size ps is 7 $\mu$m, storage time t1 is 1 msec, the maximum speed vm=7 mm/sec, and a work 4 having a chip pitch p of 10 mm and the inclination $\theta$ of the work 5 is 5°. The x-coordinate and the y-coordinate of the chips to be compared are represented by the difference pixel numbers mpx and mpy.

$$mpx = p \cdot \sin \theta / ps = 124$$

$$mpy = p \cdot \cos \theta / ps = 1423$$

where, in the case of transferring at the maximum speed, the detected pixel is square, while when transfer speed=0.8·vm, mpx=124 pixels and mpy=1423 pixels, the detected pixel is not square. To be square at the above speed, the following expressions are established:

$$mpx = (p \cdot \sin \theta / ps)(vm/v) = 155$$

$$mpy = p \cdot \cos \theta / ps = 1423$$

When $-30° < \epsilon < 30°$, the foregoing approximate expression may be used without any problem. When the range of the range of rotational phase is wider that such a range or high-accuracy control is necessary, it is preferable to produce the reference table 561 by the following method not using approximation.

$$x(m) = vm \cdot (f0/2\pi) \cdot \sin(2\pi \cdot n/f0 - \epsilon 0) + C$$

where C is an integration constant. When m=(2·l/ps)·n, mpx is calculated so as to meet:

$$x(m+mpx) - x(m) = p \cdot \sin \theta$$

in which mpy is not changed.

The reference table 561 may calculates mpx and mpy for n.

A method of controlling the storage time during detection to avoid the distortion of the image plane will be described. This method varies the storage time of the linear image sensor (detector) 40 according to a known speed curve (dx/dt) along which the speed of the work varies. This method varies the storage time so that each detected pixel is square (a figure similar to the shape of the pixel of the linear image sensor (detector) 40 when the linear image sensor (detector) 40 is not square, for example, rectangular). When the storage time is varied in proportion to the reciprocal Ti of the work scanning speed dx/dt, the vertical magnification and the transverse magnification are constant for all the points.

Figure 27B:
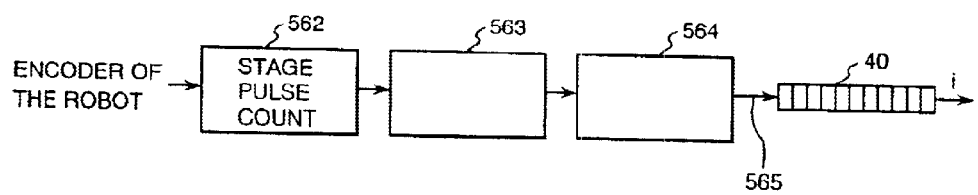
FIG. 27(b) is a block diagram for assistance in explaining the control of the accumulating time of a linear image sensor taking into consideration speed variation when transporting a wafer by a work handling mechanism (work handling robot) in accordance with the present invention.

As shown in FIG. 27(b), the position x of the work 4 is determined on the basis of the angular positions of the arms 5a and 5b of the work handling mechanism 5 detected by encoders, and an arithmetic means 563 calculates the speed dx/dt of the work 4 for each position and the accumulating time is calculated on the basis of the speed of the work 4. A timing signal generating means 564 generates a timing signal 565 on the basis of the accumulating time calculated by the arithmetic means 563 so that the signal provided by the linear image sensor 40 can be detected. An undistorted image signal i detected by using the timing signal 565 is stored temporarily in a storage 189. On the other hand, as shown in FIG. 15, the inclination $\theta$ of the work 4 is detected by an inclination detecting process 186, the coordinates of the corresponding points are produced on the basis of the detected inclination $\theta$ and the design chip pitch p, data stored in the storage 189 is fetched from the storage 189 and the corresponding points are compared by the comparing arithmetic means 190 to detect a signal 188 indicating dust particles.

Since the different image signals i are accumulated for different accumulating times, the size deviates from the true value. The deviation of the image signal i can be corrected by a method similar to the foregoing method. However, in some cases, the correction emphasizes noise. Therefore, the best data can be obtained by a method that detects signals after adjusting the inclination θ by a mechanism.

A processing apparatus for processing a work 4 having a mirror-finished surface will be described with reference to FIG. 28. Principally, a dust particle detecting system in accordance with the present invention inspects or monitors work 4 consisting of a wafer and a pattern formed on the surface of the wafer. A mirror-finished wafer not having any pattern on its surface can be inspected at a higher sensitivity than a work having a pattern thereon. Therefore, the dust particle control in the processing apparatus can be carried out by using a mirror-finished wafer. However, since the inspection of a mirror-finished wafer for dust particle takes much time including time for transporting the mirror-finished wafer from the processing apparatus, inspection cannot be carried out at a high frequency, and the mirror-finished wafer needs to be cleaned for storage.

A wafer stocker 571 for storing mirror-finished wafers 5*a* is installed in the processing apparatus, mirror-finished wafers 4*a* are transported into the processing apparatus at a specified frequency, and the surfaces of the mirror-finished wafers 4*a* are inspected by the detecting head 1*a* (1*a*') of the on-machine dust particle detecting apparatus 1 of the present invention, which solves the foregoing problems and enables dust particle monitoring at a high frequency.

The processing apparatus of the present invention comprises the wafer stocker 571, a lifting system 572, a cassette chamber 102 (103), a gate 573, the detecting unit (detecting head 1*a* (1*a*')), the work handling mechanism 5 having the arm 5*a*, a central transfer chamber 104 and a processing chamber 101. A wafer cassette 132 containing a plurality of wafers 4 of a lot, for example, twenty-five wafers or a single wafer 4*a*, is transported through the gate 573 into the transfer chamber 102 (103) and is mounted on the wafer stocker 572 so that the mirror-finished wafers 4 are parallel to each other. The wafer stocker 572 for supporting the mirror-finished wafers 4*a* may be disposed at any other suitable position provided that the arm 5*a* is able to transport the mirror-finished wafers 4*a* easily from the wafer stocker 572. The wafers 4 contained in the wafer cassette 132 are processed. The mirror-finished wafers 4 contained in the wafer stocker 572 are transported in an optional timing, more concretely, every lot (every cassette), a plurality of lots or once a day. While the wafer 4*a* is transported through an optional transport path, concretely, ordinary transport path including processing or a shortcut path, the surface of the wafer 4*a* is inspected by the detecting unit (detecting head 1*a* (1*a*')) for dust particles.

Since the mirror-finished wafers 4*a* are not cleaned very time the same are processed and returned to the wafer stocker 572, the number of dust particles on each mirror-finished wafer 4*a* increases every time the mirror-finished wafer 4*a* is processed. However, such increase does not matter, provided that the number of dust particles does not increase sharply. This monitoring calculates the difference between a dust particle distribution map (FIG. 29(*a*)) before transportation (the result of the preceding inspection) and a dust particle distribution map (FIG. 29(*b*)) after transportation to obtain detection data as shown in FIG. 29(*c*). Thus, the condition of adhesion of dust particles on the mirror-finished wafer 4*a* can be detected.

A method of monitoring dust particles adhering to the observation window of a processing chamber will be described. The inner surface of the observation window of the processing chamber may be directly detected or monitored by the detecting unit (detecting head 1*a*). Since the surfaces of the observation window are mirror surfaces, the inspection can be achieved in a high sensitivity. This monitoring method does not need any troublesome work for transporting and stocking the mirror-finished wafer 4*a* and can be carried out while the process is in operation, between processes or continuously. The detecting unit (the detecting head 1*a*) may employ a one-dimensional detector which is moved for scanning or a two-dimensional detector. The condition of adhesion of dust particles on the wafer and the dust producing condition of the processing apparatus can be estimated from the condition of adhesion of dust particles on the observation window on the basis of a database showing the relation in the condition of adhesion of dust particles between the observation window and the wafer.

The degree of contamination of the inner surfaces of the walls defining the processing chamber and the inner surface of the observation window increases gradually with the progress of processing, and the dust particle detection signal (the number of dust particles or the magnitude of the detection signal) changes accordingly. If a film deposited on the surface falls off or dust particles are produced abnormally, the dust particle detection signal changes sharply, i.e., increases or decreases sharply. In most cases, the dust particle detection signal decreases sharply when a film deposited on the surface comes off the surface. When such an abnormality is detected, the surfaces of the walls defining the processing chamber is cleaned and other necessary measures are taken.

It is desirable that the properties of the observation window are similar to those of the surfaces of the walls defining the processing chamber in respect of dust particle adhesion. Concretely, it is desirable that the temperature, the surface roughness and the quality (a metal thin film or the like is deposited on the surface) of the observation window are the same as those of the surfaces of the walls defining the processing chamber.

A shading correcting method will be described hereinafter. The surface of the work 4 must be illuminated in a uniform luminance distribution to compare signals between the adjacent chips. Generally, a laser beam has a higher luminous flux in its central portion and a lower luminous flux in its periphery and, consequently, the luminance of the middle portion of the linear field of view is higher than those of the end portions of the same. Therefore, a correcting plate is disposed in front of the cylindrical lens 34 of the illuminating optical system 31 shown in FIG. 3 to correct the luminance distribution. The correcting plate may be a plate provided with a curved slit or an ND filter having a lower transmittance in its central portion and a higher transmittance in its peripheral portion.

As is apparent from the foregoing description, according to the present invention, an alarm can be generated or warning signal can be fed back to the controller when an abnormal number of dust particles adhere to a work, such as a semiconductor wafer or a substrate on which tfts are formed when processing the work by a processing apparatus, such as a sputtering apparatus, a CVD apparatus, an etching apparatus, a resist film forming apparatus, an exposure apparatus or a cleaning apparatus, and the processing apparatus can be cleaned partially or entirely, or the processing conditions including process gas supply conditions, gas discharging conditions, temperature conditions and applied voltages can be controlled to reduce the generation of dust particles so that semiconductor devices can be produced at a high yield rate.

What is claimed is:

1. A semiconductor device producing method comprising:

measuring a condition of adhesion of dust particles adhering to a semiconductor work by a dust particle detecting apparatus positioned at least one of before and after the semiconductor work is processed by a processing apparatus disposed in a processing chamber;

managing a changing condition of incremental adhesion of dust particles to the semiconductor work being processed by the processing apparatus for each lot of works or for each work and predicting that the adhesion amount of dust particles will exceed a predetermined control limit of adhesion amount;

controlling a time or a cycle when the processing apparatus is cleaned on the basis of the managed changing condition of adhesion of dust particles for each lot of works or for each work and the predicted exceeding of the predetermined control limit; and processing the semiconductor works by the controlled processing apparatus to produce semiconductor devices;

wherein the semiconductor work is transferred by a transfer mechanism between the processing chamber in which the processing apparatus is disposed and the dust particle detecting apparatus.

2. A semiconductor device producing method according to claim 1, wherein the dust particle detecting apparatus is arranged to detect dust particles both before and after the semiconductor work is processed by the processing apparatus.

3. A semiconductor device producing method according to claim 1, wherein the dust particle detecting apparatus is provided proximate to a handling mechanism arranged between a work feed station for loading and unloading the semiconductor work and the processing apparatus so that the handling mechanism transports the semiconductor work to and from the dust particle detecting apparatus.

4. A semiconductor device producing method according to claim 3, wherein at least the dust particle detecting apparatus and the handling mechanism are disposed in a vacuum environment for the processing apparatus.

5. A semiconductor device producing method according to claim 1, wherein the dust particle detecting apparatus is located within a clean environment so that the semiconductor work is not exposed to a non-clean environment during transfer and dust particle detection.

6. A semiconductor device producing method comprising:

measuring a condition of adhesion of dust particles adhering to a semiconductor work by a dust particle detecting apparatus arranged at least one of before and after the semiconductor work is processed by a processing apparatus disposed in a processing chamber;

managing a condition of incremental adhesion of dust particles to the semiconductor work being processed by the processing apparatus for each lot of works or for each work and predicting that the adhesion amount of dust particles will exceed a predetermined control limit of adhesion amount; and processing the semiconductor works by the processing apparatus to produce semiconductor devices until the predicted exceeding of the predetermined control limit;

wherein the semiconductor work is transferred by a transfer mechanism between the processing chamber in which the processing apparatus is disposed and the dust particle detecting apparatus.

7. A semiconductor device producing method according to claim 6, wherein the dust particle detecting apparatus is arranged to detect dust particles both before and after the semiconductor work is processed by the processing apparatus.

8. A semiconductor device producing method according to claim 6, wherein the dust particle detecting apparatus is provided proximate to a handling mechanism arranged between a work feed station for loading and unloading the semiconductor work and the processing apparatus so that the handling mechanism transports the semiconductor work to and from the dust particle detecting apparatus.

9. A semiconductor device producing method according to claim 6, wherein the dust particle detecting apparatus is located within a clean environment so that the semiconductor work is not exposed to a non-clean environment during transfer and dust particle detection.

10. A semiconductor device producing method comprising:

measuring a condition of adhesion of dust particles adhering to a semiconductor work by a dust particle detecting apparatus positioned at least one of before and after the semiconductor work is processed by a processing apparatus disposed in a processing chamber;

managing a changing distribution of adhesion of dust particles to the semiconductor work being processed by the processing apparatus for each lot of works or for each work and predicting that the adhesion amount of dust particles will exceed a predetermined control limit of adhesion amount;

processing the semiconductor works by the processing apparatus to produce semiconductor devices until the predicted exceeding of the predetermined control limit; and processing the semiconductor works to produce semiconductor devices;

wherein the semiconductor work is transferred by a transfer mechanism between the processing chamber in which the processing apparatus is disposed and the dust particle detecting apparatus.

11. A semiconductor device producing method according to claim 10, wherein the dust particle detecting apparatus is arranged to detect dust particles both before and after the semiconductor work is processed by the processing apparatus.

12. A semiconductor device producing method according to claim 10, wherein the dust particle detecting apparatus is provided proximate to a handling mechanism arranged between a work feed station for loading and unloading the semiconductor work and the processing apparatus so that the handling mechanism transports the semiconductor work to and from the dust particle detecting apparatus.

13. A semiconductor device producing method according to claim 6, wherein the dust particle detecting apparatus is located within a clean environment so that the semiconductor work is not exposed to a non-clean environment during transfer and dust particle detection.

14. A semiconductor device producing method comprising:

measuring a condition of adhesion of dust particles adhering to a semiconductor work by a dust particle detecting apparatus positioned at least one of before and after the semiconductor work is processed by a processing apparatus disposed in a processing chamber;

managing a changing condition of incremental adhesion of dust particles to the semiconductor work being processed by the processing apparatus for each lot of works or for each work and predicting that the adhesion amount of dust particles will exceed a predetermined control limit of adhesion amount;

estimating causes of faults of the processing apparatus on the basis of a previously registered database indicating the relation between a dust particle distribution map showing distributions of dust particles adhering to works and corresponding causes of faults of the processing apparatus from the condition of adhesion of dust particles for each lot of works or for each work being managed when the semiconductor works are processed until the predicted exceeding of the predetermined control limit;

controlling the processing apparatus so that the estimated cause of faults is eliminated; and processing the semiconductor works by the controlled processing apparatus to produce semiconductor devices;

wherein the semiconductor work is transferred by a transfer mechanism between the processing chamber in which the processing apparatus is disposed and the dust particle detecting apparatus.

15. A semiconductor device producing method according to claim 14, wherein the dust particle detecting apparatus is arranged to detect dust particles both beforehand after the semiconductor work is processed by the processing apparatus.

16. A semiconductor device producing method according to claim 14, wherein the dust particle detecting apparatus is provided proximate to a handling mechanism arranged between a work feed station for loading and unloading the semiconductor work and the processing apparatus so that the handling mechanism transports the semiconductor work to and from the dust particle detecting apparatus.

17. A semiconductor device producing method according to claim 14, wherein the dust particle detecting apparatus is located within a clean environment so that the semiconductor work is not exposed to a non-clean environment during transfer and dust particle detection.

18. A semiconductor device producing method comprising:

measuring a condition of adhesion of dust particles adhering to a semiconductor work by a dust particle detecting apparatus positioned at least one of before and after the semiconductor work is processed by a processing apparatus disposed in a processing chamber;

managing a changing condition of incremental adhesion of dust particles to the semiconductor work being processed by the processing apparatus for each lot of works or for each work and predicting that the adhesion amount of dust particles will exceed a predetermined control limit of adhesion amount;

estimating faulty processing conditions of the processing apparatus on the basis of a previously registered database indicating the relation between faulty processing conditions for the processing apparatus and condition modes of adhesion of dust particles adhering to works from the condition of adhesion of dust particles for each lot of works or for each work being managed when the semiconductor works are processed until the predicted exceeding of the predetermined control limit;

controlling the processing conditions of the processing apparatus so that the estimated faulty processing conditions are eliminated; and processing the semiconductor works by the controlled processing apparatus to produce semiconductor devices;

wherein the semiconductor work is transferred by a transfer mechanism between the processing chamber in which the processing apparatus is disposed and the dust particle detecting apparatus.

19. A semiconductor device producing method according to claim 18, wherein the dust particle detecting apparatus is arranged to detect dust particles both before and after the semiconductor work is processed by the processing apparatus.

20. A semiconductor device producing method according to claim 18, wherein the dust particle detecting apparatus is provided proximate to a handling mechanism arranged between a work feed station for loading and unloading the semiconductor work and the processing apparatus so that the handling mechanism transports the semiconductor work to and from the dust particle detecting apparatus.

21. A semiconductor device producing method according to claim 18, wherein the dust particle detecting apparatus is located within a clean environment so that the semiconductor work is not exposed to a non-clean environment during transfer and dust particle detection.

22. A semiconductor device producing method comprising:

measuring the condition of adhesion of dust particles to a work by a dust particle detecting apparatus incorporated into a processing apparatus;

managing the changing condition of adhesion of dust particles to the work resulting from processing for each lot of works or for each work on the basis of the measured condition of adhesion of dust particles to the wafer;

estimating cleaning conditions on the basis of a previously registered database indicating the relation between a dust particle distribution map showing distributions of dust particles adhering to works and corresponding cleaning conditions from the measured condition of adhesion of dust particles to the work and a prediction of time when the managed condition of adhesion of dust particles for each lot of works or for each work indicates the increase of dust particles beyond a predetermined control limit;

cleaning the specified processing apparatus based upon predicted exceeding of predetermined control limit; and processing works to produce semiconductor devices.

23. A semiconductor device producing method comprising:

measuring the condition of adhesion of dust particles to a work by a dust particle detecting apparatus incorporated into a processing apparatus;

managing the changing condition of adhesion of dust particles to the work resulting from processing for each lot of works or for each work on the basis of measured condition of adhesion of dust particles to the work;

specifying a processing apparatus on the basis of a registered database indicating the relation between a dust particle distribution map showing distributions of dust particles adhering to works and corresponding processing apparatuses from the measured condition of adhesion of dust particles to the work and a prediction of time when the managed condition of adhesion of dust particles for each lot of works or for each work indicates the increase of dust particles beyond a predetermined control limit;

cleaning the specified processing apparatus based upon predicted exceeding of predetermined control limit; and processing works to produce semiconductor devices.

24. A semiconductor device producing system comprising:

a processing apparatus disposed in a processing chamber for processing works to produce semiconductor devices;

a dust particle detecting apparatus for measuring the condition of adhesion of dust particles to a work at least one of before and after processing the work;

a managing unit which manages the changing condition of adhesion of dust particles to a work resulting from processing for each lot of works or for each work and predicts that the adhesion amount of dust particles will exceed a predetermined control limit of adhesion amount; and a control unit which controls the time when the processing apparatus is to be cleaned or the cleaning cycle on the basis of the managed condition of adhesion of dust particles managed by the managing unit for each lot of works or for each work and the predicted exceeding of the predetermined control limit;

wherein the semiconductor work is transferred by a transfer mechanism between the processing chamber in which the processing apparatus is disposed and the dust particle detecting apparatus.

25. A semiconductor device producing system according to claim 24, further comprising a work feed station for loading and unloading works, a handling mechanism for transporting works to and from the work feed station, the processing apparatus processing works fed in and out by the handling mechanism from and to the work feed station, the dust particle detecting apparatus measuring the condition of adhesion of dust particles to a work during the transporting of the work by the handling mechanism.

26. A semiconductor device producing system according to claim 25, wherein at least the dust particle detecting apparatus and the handling mechanism are disposed in a vacuum environment for the processing apparatus.

27. A semiconductor device producing method according to claim 24, wherein the dust particle detecting apparatus is located within a clean environment so that the semiconductor work is not exposed to a non-clean environment during transfer and dust particle detection.

28. A semiconductor device producing system comprising:

a dust particle detecting apparatus for measuring the condition of adhesion of dust particles to a work for each lot of works or for each work; and a processing apparatus disposed in a processing chamber for processing works, that stops processing each lot of works or each work when an exceeding of an adhesion amount of dust particles beyond a control limit is predicted which is based upon the condition of adhesion of dust particles to the work measured by the dust particle detecting apparatus;

wherein the semiconductor work is transferred by a transfer mechanism between the processing chamber in which the processing apparatus is disposed and the dust particle detecting apparatus.

29. A semiconductor device producing system according to claim 28, further comprising a work feed station for loading and unloading works, a handling mechanism for transporting works to and from the work feed station, the processing apparatus processing works fed in and out by the handling mechanism from and to the work feed station, the dust particle detecting apparatus measuring the condition of adhesion of dust particles to a work during the transporting of the work by the handling mechanism.

30. A semiconductor device producing method according to claim 28, wherein the dust particle detecting apparatus is located within a clean environment so that the semiconductor work is not exposed to a non-clean environment during transfer and dust particle detection.

31. A semiconductor device producing system comprising:

a dust particle detecting apparatus for measuring the condition of adhesion of dust particles to a work for each lot of works or for each work; and a processing apparatus disposed in a processing chamber for processing a work, that stops processing each lot of works or each work when the condition of adhesion of dust particles to the work measured by the dust particle detecting apparatus predicts an increase of dust particles beyond a control limit and generates an alarm;

wherein the semiconductor work is transferred by a transfer mechanism between the processing chamber in which the processing apparatus is disposed and the dust particle detecting apparatus.

32. A semiconductor device producing system according to claim 31, further comprising a work feed station for loading and unloading works, a handling mechanism for transporting works to and from the work feed station, the processing apparatus processing works fed in and out by the handling mechanism from and to the work feed station, the dust particle detecting apparatus measuring the condition of adhesion of dust particles to a work during the transporting of the work by the handling mechanism.

33. A semiconductor device producing method according to claim 31, wherein the dust particle detecting apparatus is located within a clean environment so that the semiconductor work is not exposed to a non-clean environment during transfer and dust particle detection.

34. A semiconductor device producing system comprising:

a processing apparatus disposed in a processing chamber for processing works to produce semiconductor devices;

a dust particle detecting apparatus for measuring the condition of adhesion of dust particles to a work at least one of before and after processing the work;

a managing unit which manages the condition of incremental adhesion of dust particles to a work resulting from processing for each lot of works or for each work, on the basis of the measured condition of adhesion of dust particles measured at least one of before and after processing the work; and a control unit which stops the processing the work for each lot of works or for each work when the managed condition of incremental adhesion of dust particles to a work resulting from processing managed by the managing unit predicts an increase of dust particles beyond a control limit;

wherein the semiconductor work is transferred by a transfer mechanism between the processing chamber in which the processing apparatus is disposed and the dust particle detecting apparatus along a route entirely within a clean environment.

35. A semiconductor device producing system according to claim 34, further comprising a work feed station for loading and unloading works, a handling mechanism for transporting works to and from the work feed station, the processing apparatus processing works fed in and out by the handling mechanism from and to the work feed station, the dust particle detecting apparatus measuring the condition of adhesion of dust particles to a work during the transporting of the work by the handling mechanism.

36. A semiconductor device producing method according to claim 34, herein the dust particle detecting apparatus is located within the clean environment so that the semiconductor work is not exposed to a non-clean environment during transfer and dust particle detection.

37. A semiconductor device producing system comprising:

a processing apparatus disposed in a processing chamber for processing works to produce semiconductor devices;

a dust particle detecting apparatus for measuring the condition of adhesion of dust particles to a work at least one of before and after processing the work;

a managing unit which manages the changing condition of adhesion of dust particles to a work resulting from processing for each lot of works or for each work, on the basis of the measured condition of adhesion of dust particles measured at least one of before and after processing the work; and a control unit which estimates causes of faults on the basis of a previously registered database indicating the relation between a distribution adhering to works and corresponding causes of faults from the managed condition of adhesion of dust particles when the managed condition of adhesion of dust particles for each lot of works or for each work predicts an increase of dust particles beyond a control limit, and controls the processing so that the estimated causes of faults are eliminated;

wherein the semiconductor work is transferred by a transfer mechanism between the processing chamber in which the processing apparatus is disposed and the dust particle detecting apparatus along a route entirely within a clean environment.

38. A semiconductor device producing system according to claim 37, further comprising a work feed station for loading and unloading works.

39. A semiconductor device producing method according to claim 37, wherein the dust particle detecting apparatus is located within the clean environment so that the semiconductor work is not exposed to a non-clean environment during transfer and dust particle detection.

40. A semiconductor device producing system comprising:

a processing apparatus disposed in a processing chamber for processing works to produce semiconductor devices;

a dust particle detecting apparatus for measuring the condition of adhesion of dust particles to a work at least one of before and after processing the work;

a managing unit which manages the changing condition of adhesion of dust particles to a work resulting from processing for each lot of works or for each work, on the basis of the measured condition of adhesion of dust particles measured at least one of before and after processing the work; and a control unit which estimates faulty processing conditions on the basis of a previously registered database indicating the relation between processing conditions for the processing apparatus and the mode of adhesion of dust particles to the work from the measured condition of adhesion of dust particles when the managed condition of adhesion of the dust particles for each lot of works or for each work predicts an increase of dust particles beyond a control limit, and controls the processing so that the estimated faulty conditions are eliminated;

wherein the semiconductor work is transferred by a transfer mechanism between the processing chamber in which the processing apparatus is disposed and the dust particle detecting apparatus along a route entirely within a clean environment.

41. A semiconductor device producing system according to claim 40, further comprising a work feed station for loading and unloading works.

42. A semiconductor device producing method according to claim 40, wherein the dust particle detecting apparatus is located within the clean environment so that the semiconductor work is not exposed to a non-clean environment during transfer and dust particle detection.

43. A semiconductor device producing system comprising:

a processing apparatus for processing works to produce semiconductor devices;

a dust particle detecting apparatus for measuring the condition of adhesion of dust particles to a work, incorporated into the processing apparatus;

a managing means for managing the changing condition of adhesion of dust particles to a work resulting from processing for each lot of works or for each work on the basis of the measured condition of adhesion of dust particles measured by the dust particle detecting apparatus; and a cleaning means for estimating cleaning conditions on the basis of a previously registered database indicating the relation between a dust particle distribution map showing distributions of dust particles adhering to works and corresponding cleaning conditions from the measured condition of adhesion of dust particles to the work and a prediction of time when the managed condition of adhesion of dust particles to the wafer for each lot of works or for each work indicates the increase of dust particles beyond a predetermined control limit, and cleaning the processing apparatus based upon predicted exceeding of predetermined control limit under the estimated cleaning conditions.

44. A semiconductor device producing system according to claim 43, further comprising a work feed station for loading and unloading works.

45. A semiconductor device fabricating system comprising:

a processing apparatus for processing works to produce semiconductor devices;

a dust particle detecting apparatus for measuring the condition of adhesion of dust particles to a work, incorporated into the processing apparatus;

a managing means for managing the changing condition of adhesion of dust particles to a work resulting from processing for each lot of works or for each work on the basis of the measured condition of adhesion of dust particles measured by the dust particle detecting apparatus; and a cleaning means for specifying a processing apparatus on the basis of a registered database indicating the relation between a dust particle distribution map showing distributions of dust particles adhering to works and corresponding processing apparatuses from the measured condition of adhesion of dust particles to the work and a prediction of time when the managed condition of adhesion of dust particles for each lot of works or for each work indicates the increase of dust particles beyond a predetermined control limit, and cleaning the specified processing apparatus based upon predicted exceeding of predetermined control limit.

46. A semiconductor device producing system according to claim 45, further comprising a work feed station for loading and unloading works.

47. A semiconductor device producing method comprising:

measuring a condition of adhesion of dust particles adhering to a semiconductor work by a dust particle detecting apparatus positioned at least one of before and after the semiconductor work is processed by a processing apparatus disposed in a processing chamber;

managing a changing condition of incremental adhesion of dust particles to the semiconductor work being processed by the processing apparatus for each lot of works or for each work by predicting an increase of adhesion of dust particles beyond a predetermined control limit on the basis of the measured condition of adhesion of dust particles;

determining when the processing apparatus is cleaned on the basis of the predetermined increase beyond the predetermined control limit and managed changing condition of adhesion of dust particles for each lot of works or for each work; and processing the semiconductor works by the controlled processing apparatus to produce semiconductor devices;

wherein the semiconductor work is transferred between a processing chamber in which the processing apparatus is disposed and the dust particle detecting apparatus within a clean environment.

48. Semiconductor device producing method comprising the steps of:

measuring a condition of adhesion of dust particles adhering to a semiconductor work for each lot of works or for each work by a dust particle detecting apparatus; and controlling a processing apparatus disposed in a processing chamber for processing the semiconductor work so as to stop processing each lot of works or each work when the condition of adhesion of dust particles to the work measured by the dust particle detecting apparatus predicts an increase of adhesion of dust particles beyond a control limit;

wherein the semiconductor work is transferred by a transfer mechanism between the processing chamber in which the processing apparatus is disposed and the dust particle detecting apparatus within a clean environment.

49. A semiconductor device producing method comprising the steps of:

measuring a condition of adhesion of dust particles to a semiconductor work for each lot of works or for each work by a dust particle detecting apparatus; and controlling a processing apparatus disposed in a processing chamber for processing the semiconductor work so as to generate an alarm and stop processing of each lot of works or each work when the condition of adhesion of dust particles to the semiconductor work measured by the dust particle detecting apparatus predicts an increase of adhesion of dust particles beyond a control limit;

wherein the semiconductor work is transferred by a transfer mechanism between the processing chamber in which the processing apparatus is disposed and the dust particle detecting apparatus within a clean environment.

* * * * *